US009168388B2

(12) United States Patent
Rylander et al.

(10) Patent No.: US 9,168,388 B2
(45) Date of Patent: *Oct. 27, 2015

(54) SYSTEM, DEVICES, AND METHODS FOR OPTICALLY CLEARING TISSUE

(71) Applicant: Board of Regents, The University of Texas System, Austin, TX (US)

(72) Inventors: Christopher G. Rylander, Blacksburg, VA (US); Thomas E. Milner, Austin, TX (US); Oliver Stumpp, Palo Alto, CA (US); J. Stuart Nelson, Laguna Nigel, CA (US)

(73) Assignee: The Board of Regents, the University of Texas System, Austin, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/693,974

(22) Filed: Dec. 4, 2012

(65) Prior Publication Data

US 2013/0178916 A1    Jul. 11, 2013

Related U.S. Application Data

(62) Division of application No. 11/502,687, filed on Aug. 12, 2006, now Pat. No. 8,323,273.

(60) Provisional application No. 60/707,778, filed on Aug. 12, 2005.

(51) Int. Cl.
*G02C 7/10* (2006.01)
*A61N 5/06* (2006.01)
(Continued)

(52) U.S. Cl.
CPC ............... *A61N 5/06* (2013.01); *A61B 5/0066* (2013.01); *A61B 5/0068* (2013.01);
(Continued)

(58) Field of Classification Search
CPC .................... A61B 2018/00452; A61B 18/203
USPC .......................................... 607/86–94; 606/9
See application file for complete search history.

(56) References Cited

U.S. PATENT DOCUMENTS 5,000,752 A * 3/1991 Hoskin et al. ..................... 606/9
5,057,104 A   10/1991 Chess ............................... 606/9
(Continued)

FOREIGN PATENT DOCUMENTS

DE    19944401    3/2001   ............. A61B 18/12
EP    1 346 753   10/2003   ............... A61N 7/02
(Continued)

OTHER PUBLICATIONS

Chan, Eric K., et al., "Effects of compression on soft tissue optical properties" *IEEE Journal of Selected Topics in Quantum Electronics*, 2(4): 943-950 (1996).
(Continued)

*Primary Examiner* — William Thomson
*Assistant Examiner* — Jeffrey Lipitz
(74) *Attorney, Agent, or Firm* — J. Peter Paredes; David G. Rosenbaum; Rosenbaum IP, P.C.

(57) ABSTRACT

Embodiments of the present disclosure provides systems, devices, and methods for non-invasively modifying, maintaining, or controlling local tissue optical properties. Methods and devices of the disclosure may be used for optically clearing tissue, for example, for diagnostic and/or therapeutic purposes. A method of optically clearing a tissue may comprise contacting the tissue with an optical clearing device having a base, an array of pins fixed to one side of the base, a brim fixed to the base, an inlet port in the base, an exit port in the base, and a handpiece interface tab fixed to the side of the base opposite the array of pins, applying a mechanical force to the tissue, and illuminating said tissue with at least one wavelength of light through the optical clearing device. A method may further comprise controlling the temperature of the tissue illuminated.

19 Claims, 18 Drawing Sheets

(51) Int. Cl.
*A61B 5/00* (2006.01)
*A61B 18/20* (2006.01)
*A61B 18/14* (2006.01)
*A61B 18/18* (2006.01)
*A61B 17/30* (2006.01)
*A61B 18/00* (2006.01)

(52) U.S. Cl.
CPC ............ *A61B 5/0071* (2013.01); *A61B 5/0075* (2013.01); *A61B 18/203* (2013.01); *A61N 5/062* (2013.01); *A61N 5/0616* (2013.01); *A61B 5/444* (2013.01); *A61B 18/14* (2013.01); *A61B 18/1815* (2013.01); *A61B 2017/306* (2013.01); *A61B 2018/00029* (2013.01); *A61B 2018/00035* (2013.01); *A61B 2018/00452* (2013.01); *A61B 2018/00994* (2013.01); *A61N 2005/063* (2013.01); *A61N 2005/0649* (2013.01)

(56) References Cited

U.S. PATENT DOCUMENTS

| | | | |
|---|---|---|---|
| 5,143,063 A | 9/1992 | Fellner | 128/399 |
| 5,282,797 A | 2/1994 | Chess | 606/9 |
| 5,300,097 A | 4/1994 | Lerner et al. | 607/93 |
| 5,358,503 A | 10/1994 | Bertwell et al. | 606/27 |
| 5,595,568 A | 1/1997 | Anderson et al. | 606/9 |
| 5,616,140 A | 4/1997 | Prescott | 606/10 |
| 5,630,811 A | 5/1997 | Miller | 606/9 |
| 5,698,866 A | 12/1997 | Doiron et al. | 257/99 |
| 5,735,844 A | 4/1998 | Anderson et al. | 606/9 |
| 5,810,801 A | 9/1998 | Anderson et al. | 606/9 |
| 5,968,033 A | 10/1999 | Fuller et al. | 606/9 |
| 5,997,530 A | 12/1999 | Nelson et al. | 606/9 |
| 6,015,404 A | 1/2000 | Altshuler et al. | 606/9 |
| 6,059,820 A | 5/2000 | Baronov | 607/89 |
| 6,096,029 A | 8/2000 | O'Donnell, Jr. | 606/9 |
| 6,104,959 A | 8/2000 | Spertell | 607/101 |
| 6,120,497 A | 9/2000 | Anderson et al. | 606/9 |
| 6,203,540 B1 | 3/2001 | Weber | 606/15 |
| 6,273,884 B1 | 8/2001 | Altshuler et al. | 606/9 |
| 6,309,364 B1 | 10/2001 | Cathaud et al. | 601/7 |
| 6,334,074 B1 | 12/2001 | Spertell | 607/101 |
| 6,426,081 B1 | 7/2002 | Chong | 424/401 |
| 6,475,211 B2 | 11/2002 | Chess et al. | 606/9 |
| 6,508,813 B1 | 1/2003 | Altshuler | 606/9 |
| 6,511,475 B1 | 1/2003 | Altshuler et al. | 606/9 |
| 6,517,532 B1 | 2/2003 | Altshuler et al. | 606/9 |
| 6,530,920 B1 | 3/2003 | Whitcroft et al. | 606/13 |
| 6,605,080 B1 | 8/2003 | Altshuler et al. | 606/3 |
| 6,663,620 B2 | 12/2003 | Altshuler et al. | 606/9 |
| 6,770,069 B1 | 8/2004 | Hobart et al. | 606/9 |
| 6,926,683 B1 | 8/2005 | Kochman et al. | 601/118 |
| 6,974,451 B2 | 12/2005 | Altshuler et al. | 606/9 |
| 7,060,061 B2 | 6/2006 | Altshuler et al. | 606/3 |
| 7,077,840 B2 | 7/2006 | Altshuler et al. | 606/9 |
| 7,160,289 B2 | 1/2007 | Cohen | 606/9 |
| 7,331,964 B2 | 2/2008 | Maricle et al. | 606/88 |
| 2002/0128635 A1 | 9/2002 | Altshuler et al. | 606/9 |
| 2003/0055414 A1 | 3/2003 | Altshuler et al. | 606/9 |
| 2003/0187486 A1 | 10/2003 | Savage, Jr. et al. | 607/89 |
| 2004/0006332 A1 | 1/2004 | Black | 606/9 |
| 2004/0147984 A1* | 7/2004 | Altshuler et al. | 607/88 |
| 2004/0147986 A1 | 7/2004 | Baumgardner et al. | 607/94 |
| 2004/0210276 A1 | 10/2004 | Altshuler et al. | 607/88 |
| 2005/0065531 A1 | 3/2005 | Cohen | 606/88 |
| 2005/0251118 A1* | 11/2005 | Anderson et al. | 606/9 |
| 2005/0251120 A1 | 11/2005 | Anderson et al. | 606/9 |
| 2005/0251242 A1 | 11/2005 | Bousfield et al. | 607/150 |
| 2006/0084942 A1* | 4/2006 | Kim et al. | 604/890.1 |
| 2007/0088386 A1 | 4/2007 | Babaev | 606/204 |
| 2007/0149900 A1 | 6/2007 | Lin | 601/15 |
| 2007/0149991 A1 | 6/2007 | Mulholland | 606/186 |
| 2008/0060148 A1 | 3/2008 | Pinyayev et al. | 15/22.1 |
| 2008/0243039 A1 | 10/2008 | Rhoades | 601/73 |
| 2009/0287195 A1 | 11/2009 | Altshuler et al. | 606/9 |

FOREIGN PATENT DOCUMENTS

| | | | |
|---|---|---|---|
| WO | WO 96/23447 | 8/1996 | ............ A61B 17/36 |
| WO | WO 98/05286 | 2/1998 | ............ A61H 7/00 |
| WO | WO 99/46005 | 9/1999 | ............ A61N 5/06 |
| WO | WO 99/52595 | 10/1999 | ............ A61N 5/06 |
| WO | WO 2004/066899 | 8/2004 | |
| WO | WO 2005/046793 | 5/2005 | ............ A61N 5/06 |

OTHER PUBLICATIONS

Mak, Arthur F.T., et al., "A biphasic poroelastic analysis of the flow dependent subcuntaneous tissue pressure and compaction due to epidermal loadings: Issues in pressure sore" *Journal of Biomedical Engineering*, 116: 421-429 (1994).

Rylander, C, et al., "Mechanical tissue optical clearing devices: Enhancement of light penetration in ex vivo porcine skin and adipose tissue" *Lasers in Surgery and Medicine*, 40: p. 688-694 (2008).

Shangguan, H., et al., "Pressure effects on soft tissues monitored by changes in tissue optical properties" *Proc. SPIE* 3254: 366-371 (1998).

Vargas, G., et al., "Use of osmotically active agents to alter optical properties of tissue: Efects on the detected fluorescence signal measured through skin" *Lasers Surg Med* 29:213-220 (2001).

Extended Search Report issued in corresponding European Patent Application No. 13178261.7, pp. 1-13 (Sep. 27, 2013).

\* cited by examiner

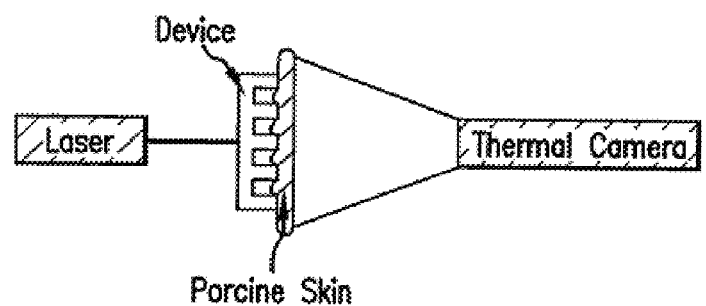
FIG. 19
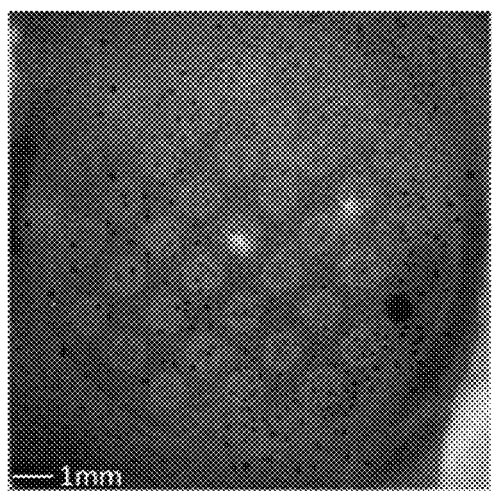
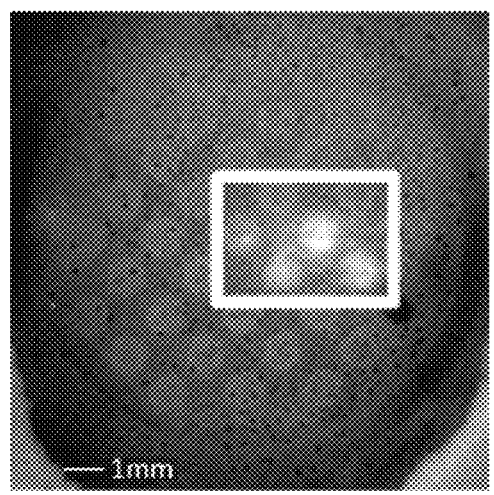
FIG. 20A          FIG. 20B

SYSTEM, DEVICES, AND METHODS FOR OPTICALLY CLEARING TISSUE

CROSS-REFERENCE TO RELATED APPLICATIONS

This application is a divisional application from U.S. patent application Ser. No. 11/502,687, filed Aug. 12, 2006, which claims the benefit of U.S. Provisional Patent Application Ser. No. 60/707,778, filed Aug. 12, 2005, all of which are incorporated herein in their entirety by reference.

STATEMENT OF GOVERNMENT INTEREST

This disclosure was supported in part by funding from the National Science Foundation, Grant Nos. 9986296 and 9870653. The U.S. Government may have certain rights in the invention.

BACKGROUND

The present disclosure relates to manipulating the optical properties of tissue for diagnostic and/or therapeutic advantage.

The specific morphology of human skin as well as other biological tissues gives rise to scattering of light. Skin may be the largest organ in the human body and composed of three distinct structures, as shown, for example, in FIG. 1. From the surface downward, they may be: 1) the epidermis; 2) dermis; and 3) subcutaneous fat (not shown). The epidermis may be the thinnest structure, varying in thickness from about 40 µm on the eyelids to about 1.6 mm on the palmar surface of the hand. The average epidermal thickness may be about 100 µm. The most superficial layer of the epidermis may be a dead outer layer, the stratum corneum, which may be responsible for the skin's chemical impermeability. Together, the stratum corneum and epidermis protect the human body from a variety of insults of physical, chemical, electrical, radiologic or microbiologic origin. The remainder of the epidermis may be a metabolically active, stratified squamous, cornifying epithelium generally populated by four types of cells: keratinocytes, melanocytes, Langerhans cells and Merkel cells in descending population frequency.

Keratinocytes form the bulk of the epidermis and undergo a specific form of cellular differentiation which may create the dead, superficial layers of the skin. Melanocytes, located in the deeper layers of the epidermis (basement membrane) may be capable of producing melanin which comprises the pigmentary system of the skin. Langerhans cells may serve an immunological function related to macrophages. Merkel cells may be receptors presumed to be involved in touch perception.

The dermis may be much thicker (1-2 mm) than the epidermis and may be subdivided into two compartments: 1) a thin zone immediately below the epidermis—the papillary dermis; and 2) a thick zone that extends from the base of the papillary dermis to the subcutaneous fat—the reticular dermis. The papillary dermis may be characterized by a network of thin (0.3-3 µm diameter) collagen fibers and elastic fibers (10-12 µm diameter), embedded in loose connective tissue and a highly developed microcirculation composed of arterioles, capillaries and venules. The reticular dermis may be composed predominantly of dense bundles of thick (10-40 µm diameter) collagen fibers that may be arranged primarily parallel to the skin's surface, interspersed among which may be coarse elastic fibers and fibroblasts embedded in an amorphous ground substance material containing water, electrolytes, plasma proteins and mucopolysaccharides. The latter consist of long-chain glycosaminoglycans which retain water in amounts up to about 1000.times. their own volume.

The scattering properties of human skin substantially constrain the development of novel approaches for both light-based therapeutics and diagnostics.

SUMMARY OF THE INVENTION

Accordingly, a need exists for systems, devices, methods, compositions, and/or kits for reducing light scattering in skin. Controlled reduction of light scattering may support a variety of light-based therapeutic and diagnostic methods and devices. A decrease in scattering strength of engineered human skin optical properties may impact light-based therapeutics by increasing the fluence delivered to a target chromophore, resulting in desired irreversible destruction. Similarly, light-based diagnostics may be improved by increasing and better localizing the coherence of the radiation stimulus at the interrogation site.

Methods and devices of the present disclosure relate to controlled modification of the optical properties of tissue and increasing light fluence at targeted chromophores. Methods and devices of the disclosure may be non-invasive, safe, and fast, may incorporate dynamic feedback, and may be physically integrated with a light delivery hand-piece. Although tissue may be contacted with a chemical clearing agent in some embodiments, such agents may be generally not required and the barrier function of the stratum corneum may be maintained (no skin abrasion or puncturing). The water transport process and optical clearing effect may be more controllable, localized, quicker, and more effective than with the use of chemical agents. In some embodiments a technique of the disclosure may also function to modulate blood volume and perfusion.

According to some embodiments, methods of the disclosure may render tissue (e.g., skin) more optically transparent for diagnostic medical imaging (e.g., OCT, Fluorescence Spectroscopy, Confocal Imaging, etc.) and therapeutic light treatments (e.g., blood vessel coagulation, hair removal, skin rejuvenation, melanoma hyperthermia, adipose contouring, removal, or reduction, and fat reduction). Depending on the form of the mechanical device which may vary the geometry of the tissue-device interface, light may be administered uniquely to the tissue (such as from the side or two sides), aiding in techniques such as hair removal, adipose contouring, removal, or reduction, and fat reduction.

According to some embodiments, an optical clearing device may comprise a mechanical transducer having a base with at least two opposing sides; an array of pins fixed to one side of the base; a brim fixed to the same side of the base as the pins; an inlet port in the base in fluid communication with both sides of the base; an exit port in the base in fluid communication with both sides of the base; and a handpiece interface tab fixed to the side of the base opposite the array of pins, wherein at least one pin in the array of pins (a) has a sapphire lens fixed to its tip and (b) is surrounded by a thermally conductive sleeve. The sleeve may be attached to the base or the base of the pin and may, together with the thermally conductive sleeve and the sapphire lens, define an air gap.

The methods, systems, and apparatuses are set forth in part in the description which follows, and in part will be obvious from the description, or can be learned by practice of the methods, apparatuses, and systems. The advantages of the methods, apparatuses, and systems will be realized and attained by means of the elements and combinations particularly pointed out in the appended claims. It is to be understood that both the foregoing general description and the following detailed description are exemplary and explanatory only and are not restrictive of the methods, apparatuses, and systems, as claimed.

BRIEF DESCRIPTION OF THE DRAWINGS

Some embodiments of the disclosure may be understood by referring, in part, to the following description and the accompanying drawings, wherein:

FIG. 19 is a schematic diagram illustrating the experimental setup with a thermal camera according to an embodiment of the disclosure.

FIG. 20A is a thermal image illustrating preferential heating of hair follicles under pins, wherein the hair follicle and epidermal heating have been enhanced by improved 980 nm light transported through in vitro porcine skin facilitated by Example Device No. 1.

FIG. 20B is a thermal image illustrating increased epidermal melanin heating, wherein the hair follicle and epidermal heating have been enhanced by improved 980 nm light transported through in vitro porcine skin facilitated by Example Device No. 1.

DETAILED DESCRIPTION OF THE INVENTION

The foregoing and other features and advantages of the invention are apparent from the following detailed description of exemplary embodiments, read in conjunction with the accompanying drawings. The detailed description and drawings are merely illustrative of the invention rather than limiting, the scope of the invention being defined by the appended claims and equivalents thereof.

Skin may act as a highly scattering medium for visible to near-infrared wavelengths due to its complex and inhomogeneous morphological structure. Light scattering in biological tissues may be caused primarily by variation in polarizability, which may be characterized by variations of the optical index of refraction n. This mismatch may be largely a function of shape, size and distribution of tissue constituents such as collagen (70% of dry weight of dermis), lipids, water, cells and their organelles, which all have slightly different indices of refraction as shown in Table 1. While the variations of optical index of refraction $\nabla n$ give rise to scattering, strength and direction of scattered light depends on size and shape of the scatterers. Light scattering from structures with size much smaller than the wavelength $\lambda$ of incident radiation is governed by Rayleigh theory. Alternatively, light scattering from structures with size comparable to the wavelength $\lambda$ of incident radiation is governed by Mie theory. In the epidermis, melanin granules and keratinocyte and melanocyte nuclei provide large $\nabla n$ that give rise to Rayleigh and Mie scattering. In the papillary and reticular dermis, Mie scattering may be due to $\nabla n$ at the interface between high-index collagen fibers and surrounding low-index extracellular fluid, ground substance and cytoplasm.

TABLE 1

Optical index of refraction of different tissue constituents

| Tissue/Cell Component | Refractive Index |
|---|---|
| water | 1.33 |
| collagen | 1.43 |
| hydrated collagen | 1.53 |
| dehydrated melanin | 1.7 |
| stratum corneum | 1.55 |
| adipose tissue | 1.46 |
| extracellular fluid | 1.35 |
| cytoplasm | 1.37 |
| nucleus | 1.39 |
| mitochondria | 1.42 |

Figure 1:
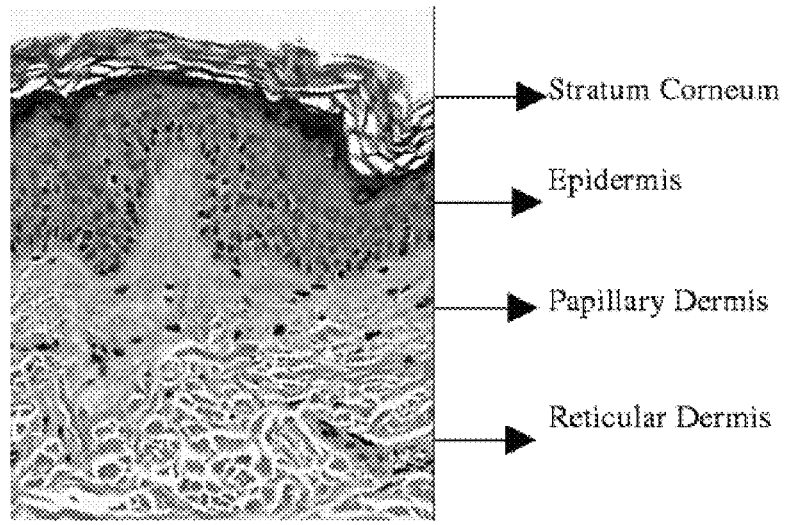
FIG. 1 illustrates the morphology of human skin.
Figure 2:
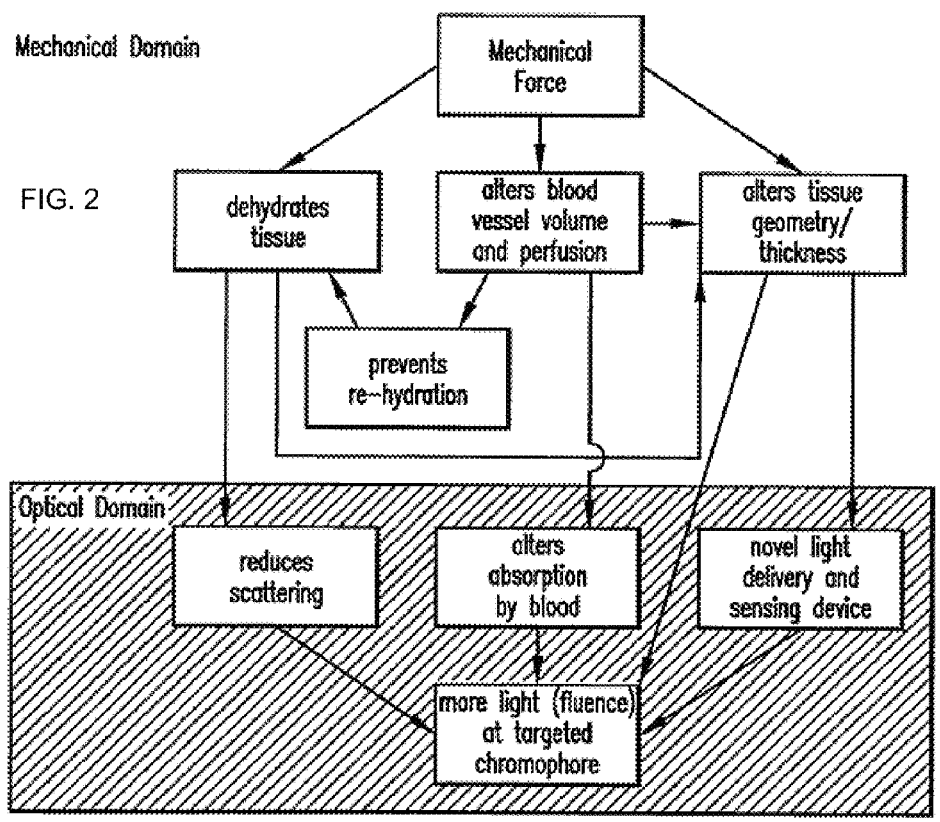
FIG. 2 is a block diagram illustrating a process of events caused by mechanical force on tissue and resulting in desirable optical domain effects according to an embodiment of the disclosure.
Figure 3A:
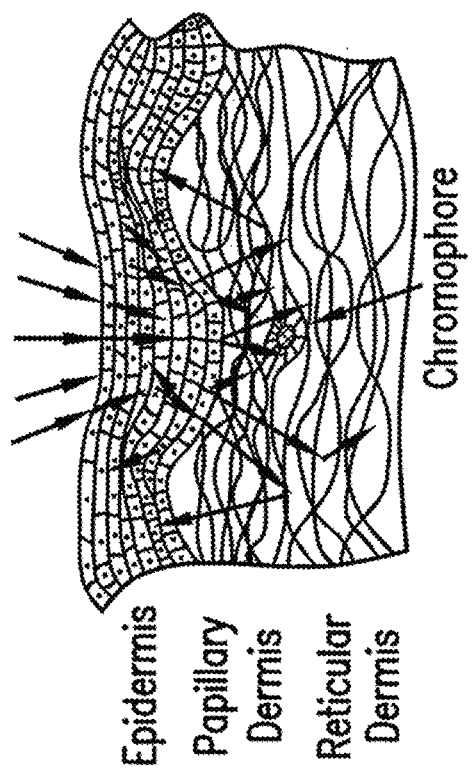
FIG. 3A illustrates a light-based therapeutic embodiment of the disclosure without optically engineered human skin.
Figure 3B:
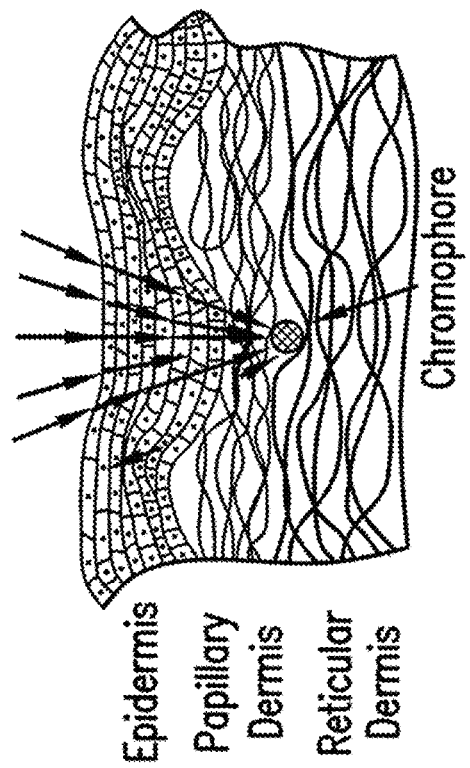
FIG. 3B illustrates a light-based therapeutic embodiment of the disclosure with optically engineered human skin in which light scattering may be reduced and increased fluence may be delivered to the target chromophore.

There may be a natural gradient of water content as a function of depth throughout skin. At the stratum corneum, water content may depend on atmospheric humidity and may be as low as about 15% and increase with depth. At a depth of about 35 μm the water content of epidermis and dermis may reach about 70%. Thus water, with its lower optical index of refraction contributes significantly to the index of refraction mismatch $\nabla n$ giving rise to light scattering. The penetration depth of light may be limited due to attenuation, which results from light scattering and light absorption within biological tissue. Significant tissue chromophores that absorb laser energy in skin may include water, melanin and hemoglobin in blood. In light-based therapeutics, successful treatment outcome may require a temperature increase by absorption of incoming photons. Specifically, successful treatment outcome may depend on a desired temperature increase in selected tissue regions resulting in destruction of targeted chromophores, while maintaining temperature below the threshold for destruction in non-targeted tissue regions (FIG. 2).

Temperature increase $\Delta\Delta T (r, z)$ in tissue at position $(r, z)$ may be given by, $$\Delta T = \frac{\mu_a \cdot \Phi}{\rho \cdot c}$$

and may be dependent on tissue absorption coefficient ($\mu_a$), optical fluence $\Phi$ and tissue heat capacity $\rho \cdot c$. In tissue regions targeted for destruction, desired temperature increase may be obtained by either increasing $\mu_a$ or $\Phi$ or decreasing $\rho \cdot c$ or some combination thereof. For example, tissue absorption coefficient $\mu_a$ may be increased at a selected position by increasing chromophore density at that position. Fluence $\Phi$ may be increased at a given position $(r_O, z_O)$ by decreasing tissue scattering at overlying positions $(z<z_O)$. The tissue heat capacity $\rho \cdot c$ may be decreased by reducing water concentration. Likewise, in tissue regions not targeted for destruction, temperature increase may be lessened by either decreasing $\mu_a$ or $\Phi$ or increasing $\rho \cdot c$ or some combination thereof.

TABLE 2

Pathologic conditions amenable to light-based therapies

| Vascular Lesions | Pigmented Lesions | Other Skin Pathologies |
| --- | --- | --- |
| Hirsutism | Cellulite | |
| Port Wine Stains (PWS) | Lentigo | Skin cancers PDT |
| Hemangiomas | Nevus of Ota | Acne vulgaris |
| Telangiectasis | Nevus of Ito | Acne scars |
| Angiomas | Blue nevus | Hypertrophic scars |
| Adenoma sebaceum | Ephelides | Rhytides |
| Angiokeratomas | Becker's nevi | Hypertrichosis |
| Venous lakes | Hairy nevi | Hidradenitis suppurative |
| Spider veins | Epidermal melanosis | Pseudo-folliculitis barbae |
| Rosacea | Nevus spilus | Tattoos |
| Poikloderma of Civatte | Hyper-pigmentation | Chrysiasis |
| | | Adipose contouring |
| | | Adipose removal |
| | | Adipose reduction |

Light-based diagnostics and/or therapeutics may benefit from reduced human skin light scattering by two different pathways: 1) increased effective fluence that reaches the target chromophore; and 2) reduced overall backscattered light from the dermis reaching non-targeted chromophores such as melanin in the epidermis which increases the latter's threshold for injury.

This may be particularly important in patients with darker skin types where it may not be possible to target chromophores with sufficiently high therapeutic dosage due to non-specific epidermal damage. Taken together, reduced light scattering and re-distribution of tissue chromophores may not only make light-based therapeutic procedures more effective, but also safer. A review of some pathologic conditions amenable to light-based therapies that may benefit from optically engineered human skin is provided in Table 2.

Port wine stain (PWS) may be a congenital, progressive vascular malformation of skin that occurs in an estimated 4 children per 1,000 live births. Approximately 1,500,000 individuals in the United States and thirty-two million people worldwide have PWS birthmarks. Since most of the malformations occur on the face, PWS may be a clinically significant problem in the majority of patients. To some extent, PWS may be considered a cosmetic problem, but it may also be regarded as a disease with potentially devastating psychological and physiological complications. Personality development may be adversely influenced in virtually all patients by the negative reaction of others to a "marked" person. Detailed studies have documented lower self-esteem in such patients and problems with interpersonal relationships. Studies have indicated a high level of psychological morbidity in PWS patients resulting from feelings of stigmatization that may be frequently concealed in casual social interactions. In childhood, PWS may be flat red macules, but lesions tend to darken progressively to purple, and by middle age, often become raised as a result of the development of vascular nodules. Hypertrophy of underlying soft tissue, which occurs in approximately two-thirds of lesions, further disfigures the facial features of many patients.

Histopathological studies of PWS show a normal epidermis overlying an abnormal plexus of dilated blood vessels located in the dermis. PWS blood vessel diameter (30-300 µm) and depth distribution (200-750 µm) vary on an individual patient basis and even between different areas on the same patient. Pulsed dye laser (PDL) treatment, which may selectively destroy dermal blood vessels, typically results in a variable and unpredictable degree of blanching. If the ultimate standard required may be complete blanching of the lesion, the average success rate may be below 10%, even after undergoing multiple PDL treatments. Without limiting the disclosure to any particular theory or mechanism of action, this may occur because of the inability to deliver an adequate effective light fluence to the targeted PWS blood vessels.

Methods and devices of the present disclosure may reduce light scattering and redistribute tissue chromophores in optically engineered human skin, for example, in combination with PWS laser therapy. In some embodiments, methods and devices of the disclosure may increase the therapeutic success rate, improve safety, and/or decrease the number of repeat treatments as follows:

1. Reduced light scattering may permit safe and effective laser treatment of PWS by increasing the threshold for epidermal damage. The best clinical results in patients with PWS undergoing laser therapy may be obtained when the ratio of heat generated in blood vessels to that in the epidermis may be highest.

2. For patients with darker skin types, previous methods did not permit treating lesions with a sufficiently high therapeutic light dosage due to epidermal damage. Reduced light scattering and localized reduction of melanin concentration due to skin stretching may expand the population of patients expected to benefit from laser therapy by increasing the threshold for epidermal damage.

3. A principal reason for poor clinical results seen after laser therapy of patients with PWS may be insufficient heat generation within large blood vessels. Multiple treatments at low light dosages will not achieve and sustain the critical temperature necessary to destroy irreversibly large blood vessels, regardless of the number of treatments performed. Optically cleared skin may permit the use of higher incident light dosages to produce higher intravascular temperatures, over longer periods of time without producing permanent complications such as hypertrophic scarring, changes in skin pigmentation, atrophy, or induration.

Without being limited to any particular mechanism of action, reduction of light scattering may be achieved by three mechanisms, which include local tissue dehydration, index of refraction matching and structural modification of proteins such as collagen. Local tissue dehydration may cause tissue shrinkage and bring individual scattering centers closer together, thereby reducing light scattering in highly turbid skin.

Optical skin clearing induced by delivery of hyper-osmotic agents such as glycerol or dextrose may be hindered since these agents typically diffuse poorly across the natural skin barrier formed by the stratum corneum. Furthermore, modification of the barrier by thermal, chemical or mechanical means requires additional time beyond diffusional mass transport. Consequently, maximum optical skin clearing has been observed, in some cases, at approximately 60 to 360 minutes after the application of the optical skin clearing agent.

Mass transport of interstitial water resulting in a re-distribution of this abundant tissue chromophore may be induced by osmotic stress. However, more efficient may be mechanical displacement and re-distribution of interstitial tissue water.

The present disclosure provides, in some embodiments, a device for controlled local (fractional) tissue dehydration and/or local skin compression and stretching resulting in redistribution of the most significant tissue chromophores including water, blood and melanin.

Without being limited to any particular mechanism of action, specific example embodiments of the disclosure may involve applying at least one mechanical force to a tissue (e.g., skin) to increase light transport to targeted chromophores and/or increase or decrease selected chromophore concentration in tissue. Application of a mechanical force may move intracellular and interstitial water out of a targeted tissue volume causing spatial redistribution of one or more scatterers and thereby reduce light scattering. Application of a mechanical force may increase or decrease blood volume fraction and perfusion and/or may modulate one or more natural mechanisms for maintaining tissue hydration. Application of a mechanical force may increase or decrease tissue volume or thickness.

Example embodiments of this disclosure may include a feedback device that provides a distribution of mechanical forces to skin for improved laser treatment of a variety of conditions, e.g., hair removal, blood vessel coagulation, skin rejuvenation, adipose contouring, adipose reduction, and adipose removal. An embodiment of a method of the disclosure applied to skin may comprise applying a lifting force (e.g., hypobaric pressure) that positions a tissue volume within a control volume of a device having one or more surfaces for applying a mechanical force to the tissue. A method of the disclosure may further comprise injecting light into the control volume and light sensors that provide a feedback signal to the mechanical force transducers. Using the feedback signal, the mechanical force transducers may be configured to provide optimal light fluence at the targeted chromophores.

Techniques and devices of the disclosure may increase the probability of chromophore damage by increasing light fluence at the targeted chromophore. The device may accomplish this task by redistributing chromophores such as intracellular and interstitial water, blood and melanin, by decreasing the physical thickness of tissue, and by employing a light delivery and optionally a sensing methodology. Methods and devices of the disclosure may improve both optically based therapeutic and diagnostic procedures. The block diagram in FIG. 2 illustrates the events, according to some embodiments, associated with applying mechanical force on tissue and resulting in desirable optical domain effects.

As will be apparent to one of ordinary skill in the art, there may be numerous functional elements that may be potentially embodied with different structure in devices of the disclosure. Some non-limiting examples of these are listed in Table 3.

According to some embodiments of the disclosure, a system may comprise synergistic functional elements and structural embodiment including, without limitation, (1) a radiant source, (2) a mechanical transducer, (3) a tissue position and hold mechanism, (4) a radiant filter, (5) a cooling system, (6) a feedback system between a tissue and a radiant source, and (7) tissue to be treated.

(1) Radiant Source

The radiant source generates electromagnetic energy that will ultimately be delivered to targeted tissue chromophore(s). This functional element may be structurally embodied as a laser, incoherent source (flashlamp), light emitting diode (LED), radio frequency, microwave, or x-ray source.

For example, a laser source may, in some embodiments, provide a dosimetry (e.g., wavelength, fluence, pulse duration, and/or spot size) that may be selected to target specific structures and/or material compositions in a tissue. In some embodiments, a tissue may be targeted by using the principles of selective photothermolysis.

(2) Mechanical Transducer

A mechanical transducer may apply force to the tissue that alters the tissue's mechanical state (e.g., thickness, stress, and strain) and optical properties. The tissue scattering coefficient may be modified by displacement of water and may result in increased density of scatterers. The tissue absorption coefficient may be modified by displacement/concentration alteration of chromophores. Additionally, tissue compression may improve radiant throughput by reducing the path length to a target in the tissue. Tissue compression may be fractional in some embodiments. For example, compression may occur at discrete points that constitute less than the total area enclosed by the brim.

In some embodiments, a mechanical transducer may include an array of pins that contact target tissue. Alternatively, a mechanical transducer may be embodied as a clamp, where two surfaces (pinned or flat) may be forced together with tissue in-between. In this embodiment, a tissue volume may be positioned between two surfaces either of which contain mechanical transducers such as a pin array. Application of a clamping force (e.g., spring, screw, piston, pneumatic) forces the pins into the tissue, displacing water and modifying tissue optical properties.

TABLE 3

Functional Elements of the Disclosure

| Functional Elements | Structure | | | | |
|---|---|---|---|---|---|
| Radiant Source | Laser | Radio Frequency | Microwave | X-ray | Incoherent Light Source (e.g. LED or flashlamp |
| Mechanical Transducer | Pins | Vacuum | Clamp | Rolling Cylinder w/ Pins | |
| Radiant Filters | Mask | Conventional Lens | Fresnel Lens | Holographic Lens | Hybrid Lens |
| Cooling | Conduction in Pins | Convective Liquid (e.g. against pins, tissue, or base) | Convective Gas against (e.g. against pins, tissue, or base) | Evaporative Liquid against (e.g. against pins, tissue, or base) | |
| Feedback of Optical Properties to Source | Optical Feedback | Ultrasonic Feedback | Mechanical Feedback | Electrical Feedback | |
| Tissue Position and Hold | Vacuum Device | Clamp | | | |
| Tissue and Chromophores | Melanin | Hemoglobin | Water | Dye | Lipid or Fat |

In some embodiments, a mechanical transducer may include one or more sub-components selected from the group consisting of an array of pins, a brim, a base, an inlet and exit port and tubing, and a handpiece interface tab. In some embodiments, apart from the inlet and exit port tubing, the device may be constructed in a single manufacturing process using a single material. The device may be constructed of a variety of materials transparent to incident radiant energy such as glass, clear polymer, or similar optical material so radiant energy may be applied to the tissue while the device may be in position and functioning. A thermally conductive material, such as sapphire, may be desirable to aid in the tissue cooling function. Inlet and exit port tubing may consist of commercially manufactured polymer hose. The device may be manufactured through thermoplastic molding or machining.

An example device of the disclosure may include a clear plastic resin, may be circular in shape, and may have a diameter of about 1.5 cm. The device shown in FIG. 4 features an outer brim, which acts as a seal once the device is placed onto the skin surface.

(a) Array of Pins

Inside, facing the skin surface may be an array of pins, which may be constructed of a variety of optically transparent materials such as glass, clear polymer, or similar optical material so radiant energy may be applied to the tissue while the device is in position. While pins may be generally firm or rigid, in some embodiments, an array of pins may include at least one pin that may be resilient. An array of pins may be manufactured using known procedures including thermoplastic molding or machining.

Pin design parameters may include pin shape (e.g., flat, rounded), diameter, length, packing density, tip shape, arrangement, and number. Pins may be shaped as cylindrical rods, as shown in FIG. 4, or with many other cross-sectional shapes (e.g., triangular, square, radial, or spiral). Pin diameter may be selected according to flux of water transport in response to tissue compression. Pin diameters on the order of 0.5 to 1.0 mm may provide fast (1-5 s) response of tissue optical property change. Smaller pin diameters may give faster water transport and more rapid change in tissue optical properties. However, the artisan of ordinary skill may, according to some embodiments, balance small pin diameter against a reduced applied pressure corresponding to risk of tissue penetration or puncture. In some embodiments, pin length may be sufficiently large to prevent skin contact with the device base and possible blockage of the inlet or exit port. Pin length of about 2-3 mm may be sufficient for a pin packing density greater than 20%. Density in this respect refers to the cross-sectional area of the pins at their tips as a fraction of the area defined by the anterior perimeter of the brim. A pin cross section for density calculation may also be at the base or midpoint. Pins on a single device may have a uniform length or from 2 to Q different lengths, where Q is the number of pins on the device.

Modification of local tissue optical properties may be more effective and rapid with low pin packing density, but the fractional area of compressed tissue may be diminished. Pin packing densities of 20-50% have been implemented successfully on some example devices. Pin tip shape (e.g., hemispherical, flat, conical) may simultaneously affect the stress profile in tissue and serve as a radiant filter. A hemispherical-shaped pin tip may distribute stress more uniformly in tissue, provide enhanced and rapid alteration of tissue optical properties, and simultaneously act as a lens embodiment of a radiant filter. A sapphire ball lens may be used to form a hemispherical-shaped pin tip that additionally provides a high conductivity path for thermal energy removal from the tissue just beneath the pin. A flat or planar-shaped pin tip may induce a ring of high tissue stress along the circumference of the pin tip, and may not induce a lensing effect. Pins may be arranged in many lattice geometries including, without limitation, uniformly (e.g., in a Cartesian grid, a checker-board pattern, a hexagonal pattern), haphazardly, or randomly distributed. The total number of pins, effective pin size, and pin packing density may determine the total size of the pin array. The pin array may be large enough to accommodate the entire cross-sectional area of the incident radiant source, and small enough to form a seal (e.g., hypobaric or pneumatic) with a curved tissue surface such as external facial structures. A pin array diameter on the order of 1-2 cm may be appropriate in some embodiments.

(b) Brim

A brim of a mechanical transducer may be the lip along the periphery of the device which may form an airtight or vacuum seal with the tissue surface. A brim may completely surround and enclose an array of pins. The shape of the brim may be coupled with the shape of the pin array. A brim may be laterally offset from the edge of the pin array by approximately 1-2 mm, e.g., to ensure an airtight seal. The length and width of a brim may be approximately the same as that of the pins (e.g., 1 mm). Shape of the brim tip that interfaces with skin may be circular, according to some embodiments, since this shape may conform with the tissue quickly and seal effectively.

(c) Base

A base of a mechanical transducer may be, in some embodiments, a flat plate which supports both the pins and the brim. The base may also provide a support structure for radiant filters. According to some embodiments, a base may be at least 2-3 mm thick in order to provide structural strength and rigidity of the device. In other embodiments, a base may be made of, for example, a flexible, resilient, and/or elastomeric material. A flexible base may permit, for example, an adjoining array of pins to better adopt the contours of a surface (e.g., tissue) with which it is contacted.

(d) Inlet and Exit Port and Tubing

Inlet and exit ports may permit the flow of fluid into and exiting the chamber (which may be formed when the device is applied to tissue). An inlet may include a single aperture or an array of apertures in the base. Similarly, an exit port may include a single aperture or an array of apertures in the base. In addition, port holes may be surrounded by a connector (e.g., a Luer fitting) extending about 3-5 mm from the posterior surface of the device base. Port tubing may be fastened to the device by compression into the port holes, or by expansion around Luer fittings. Inlet and exit port tubing may include, without limitation, commercially manufactured polymer hose.

(e) Handpiece Interface Tab

Figure 6B:
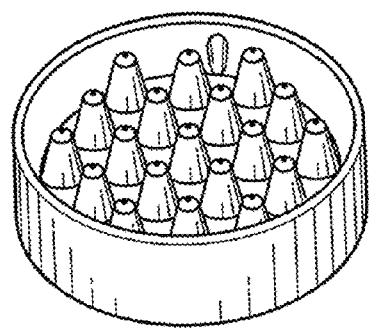
FIG. 6B illustrates an example embodiment of an array of pins corresponding to the radiant filters, wherein the array defines an inner surface of the optical clearing device and may contact and/or apply a mechanical force on the skin.
Figure 6D:
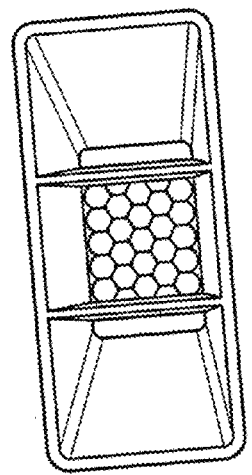
FIG. 6D illustrates an example embodiment of inlet and exit ports of an optical clearing device which may permit integration of vacuum and cooling systems with the device and tissue surface.
Figure 6A:
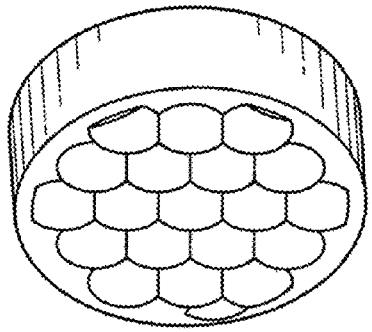
FIG. 6A is an isometric drawing (posterior surface on the left) of an example embodiment of radiant filters in an optical clearing device which may used to control spatial and angular distribution of incident radiant energy into targeted tissue regions.
Figure 6C:
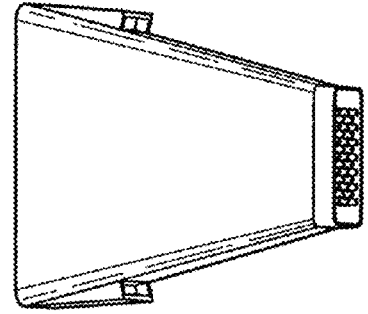
FIG. 6C illustrates an example embodiment of handpiece interface tabs of an optical clearing device which may provide a mechanical linkage between the device and the laser handpiece.
Figure 6E:
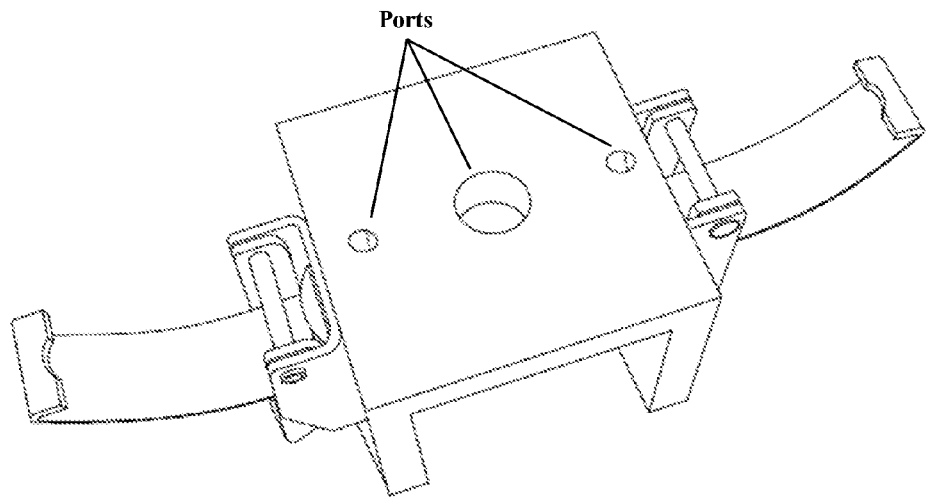
FIG. 6E illustrates the handpiece interface including a draw latch and keeper system.
Figure 6F:
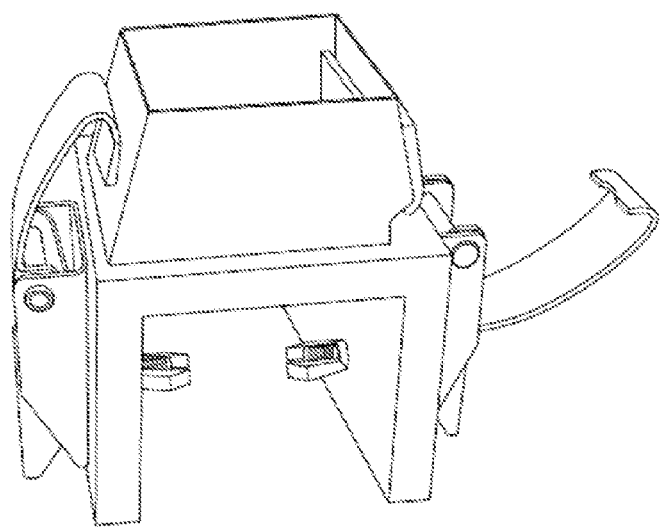
FIG. 6F illustrates the handpiece interface mechanically linked to the handpiece interface tabs of the optical clearing device.

A handpiece interface tab may provide a mechanical linkage between a mechanical transducer device and a radiant source, as shown in FIGS. 6C, 6E, and 6F. For example, a handpiece interface tab may be structurally embodied as a tab with a flanged or curved tip. A user may press (or twist) a device against a radiant source handpiece, and the flanged or curved tip may be locked into a handpiece receptacle. When desired, a user may remove the device from the handpiece by gently forcing or twisting them apart.

(3) Tissue Position and Hold Mechanism

A tissue position and hold mechanism may facilitate alignment of the mechanical transducer element against the tissue and formation and/or maintenance of an airtight seal if a pneumatic embodiment is employed. A primary embodiment for the tissue position and hold mechanism may be a hypobaric vacuum chamber. In this embodiment an applied hypobaric pressure determines the vertical position of the tissue with respect to the mechanical transducers (e.g., array of pins). The tissue position and hold function may be structurally embodied with a pin array surface and/or vacuum device.

A pneumatic device may aid in the mechanical transduction process by forcing the tissue against the pins while simultaneously pulling tissue into the volume surrounding each pin (i.e., control volume). The increased tissue volume surrounding the pins (expanded tissue regions) provides additional storage capacity for water and blood displaced from under the pins. A pneumatic device may include a vacuum pump and a hose connecting the pump to the pin array device (e.g., exit port).

(4) Radiant Filters

The radiant filters may be utilized to control spatial and angular distribution of incident radiant energy into targeted tissue regions. The radiant filters and their spatial arrangement may be engineered specifically for each treatment application. For example, radiant filters may be used to direct radiant energy to mechanically compressed regions for hair removal, skin rejuvenation or adipose reduction treatments because scattering coefficient may be reduced (optimized) and water concentration may be reduced (optimized) in these regions. Radiant energy may be directed into the expanded tissue regions for blood vessel coagulation treatments because chromophore density may be highest (optimized) in these regions. The radiant filter function may provide an important accessory function, namely, spatial control of optical fluence and therapeutic modification of the tissue. Radiant filters may be structurally embodied using a mask (absorptive or reflective) or lenses on the anterior and/or posterior side of the pin array device (conventional, fresnel, holographic, or hybrid). For example, an absorptive or reflective mask may consist of a layer of radiant energy absorbing or reflecting dye or metal painted on either surface of the mechanical transducer. In another embodiment, a spherical surface above the pin (air-material interface) may serve as a radiant filter. Similarly, the posterior pin surface in contact with the tissue surface may also serve as a lens radiant filter. For example, a posterior pin may include a sapphire ball lens as a high thermal conductivity radiant filter. Lenses may permit angular control (focusing or divergence) of radiant energy incident on the tissue and/or allow light to be directed to a desired tissue area and/or tissue depth.

(5) Cooling System

A cooling system may provide tissue surface cooling and/or may prevent thermal damage of non-targeted, superficial layers before, during, or after the tissue contacts radiant energy. A cooling system may be applied prior to radiant emission into the tissue, during radiant emission into the tissue, and after radiant emission into the tissue. In one embodiment, the cooling system may use a convective liquid or gas forced against the targeted tissue (or pin surfaces) using a high-pressure (inlet) or low-pressure (outlet) source. An electronically controlled solenoid valve may be utilized to control the flow of liquid or gas into the control chamber and to the tissue (pin) surface thereby regulating tissue temperature profile. An example of a high-pressure inlet source may be compressed, reduced temperature, dry air. An example of a low-pressure outlet source may be a pneumatic device that may also serve as a mechanical transducer.

In a second embodiment, tissue cooling may be performed by conducting heat away from the tissue through a pinned surface. In this embodiment, it may be desirable to have a highly thermally conductive transparent material such as sapphire. In this embodiment the tip of the pin may be a highly thermally conductive material (e.g., sapphire) that is in thermal contact with a highly thermally conductive sheath or thin-wall tube surrounding the pin. Thermal conductivity of a highly thermally conductive transparent material, in some embodiments, may be over about 0.3 $Wcm^{-1}K^{-1}$ and/or may be over about 0.45 $Wcm^{-1}K^{-1}$. A highly thermally conductive sheath or thin-walled tube surrounding a pin may be a metallic material such as aluminum. In this embodiment, a sheath or thin-walled tube and a pin may be configured and arranged to define an air gap. An air gap may permit better containment of light in a pin. Thermal energy conducted from the tissue into the tip of the pin and into the thermally conductive sheath surrounding the pin may be removed from the thin-walled tube by, for example, convective liquid or gas, a liquid-solid slurry or by an evaporative liquid.

In a third embodiment, deposition and evaporation of an evaporative liquid on the tissue surface may provide the cooling function.

When selecting temperature of the thermal fluid, duration of application of the thermal fluid and whether simultaneous radiant heating is occurring may be considered. For example in the precooling step (cooling before radiant exposure), temperature of the thermally-controlled fluid may be −50° C. if the duration of tissue contact is sufficiently short (e.g., less than 100 ms). Accordingly, thermal fluids with a higher temperature (−10° C.) can be applied for longer times (200 ms).

During radiant exposure, temperature of the thermal fluid may be determined in part by the effective heat transfer coefficient between the tissue and fluid, and heat transfer coefficient between the thermal fluid and the pin, and rate of temperature increase due to absorption of radiant energy in the tissue. In this step, temperature of the cooling fluid may be reduced below 0° C. (e.g., −10° C.) in order to remove thermal energy from tissue regions not targeted for damage. In cases when a substantially higher heat transfer out of the tissue through the pin is desired, a thermally insulating material (polymer) may be placed between the tissue (tissue region not in contact with the pin) so that thermal fluids with very low temperatures (−50° C.) may be used over long periods of time (e.g., up to about 30 seconds).

The operating principle in selecting a temperature of the thermally-controlled fluid in the pre-cooling and radiant exposure steps may be, according to some embodiments, that the temperature reduction during pre-cooling and subsequent radiant exposure in tissue regions not targeted for damage does not result in either nonspecific cryo- or thermal-injury.

The temperature of a thermally-controlled fluid may be below about −150° C., between about −150° C. and 40° C., between about −150° C. and 0° C., between about 0° C. and 40° C., between about 27° C. and 47° C., between about 28° C. and 43° C., or over 40° C.

(6) Feedback System Between Tissue and Radiant Source

Measurement of optical properties may provide a feedback signal to the cooling system and the radiant source for delivering the radiant energy dosage to the targeted tissue. The feedback system may control the radiant energy dosimetry including pulse duration, energy, and start time of exposure. The feedback system may utilize optical or mechanical sensors. An optical feedback system may utilize the radiant source used for treatment or an alternative radiant source. Similarly an optical feedback system may utilize the radiant filters used for treatment or radiant filters specialized for the feedback system.

A mechanical feedback system may utilize a pressure gauge in a hypo- or hyperbaric pressure source. In addition a mechanical feedback system may incorporate specialized pressure, stress, or strain sensors dedicated to the feedback system. Alternatively, the feedback system may utilize ultrasonic or electrical sensors.

A feedback system may control, for example, temperature and/or flow of a thermally-controlled fluid. For example, a feedback sensor may be configured to sense tissue heating and signal a controller or control to intensify cooling and/or reduce the intensity of radiation.

(7) Tissue to be Treated

Tissue chromophores may be targeted elements in the tissue which absorb the radiant energy. Absorption of radiant energy may induce tissue therapeutic modification through photothermal, photoacoustic, or photochemical processes. The chromophores may be native tissue structures such as water, melanin or hemoglobin (blood), lipids (adipose), or synthetic such as a photodynamic dye.

Operation

A hypobaric pressure (e.g., up to about 750 mm Hg) may be applied through a small vacuum hose connected to the back side of the device.

Once the device is applied to the skin surface and the vacuum is established, skin may be positioned against the pins and compressed under individual pins. As the skin molds around the pins, tissue may become stretched and melanin concentration underneath each pin may be reduced.

Due to the mechanical pressure under each pin, tissue water may be mechanically displaced by diffusive transport with a coefficient of 1 to 1.5 mm$^2$/s. Due to the lower pressure surrounding the pins, tissue volume may be increased and displaced water collects in the tissue surrounding the pins.

After positioning of the tissue against the pins, a first cooling step may be performed to reduce the temperature in the tissue below the pins and adjacent to the pins. The reduced temperature distribution in the tissue may be controlled by the time duration of applied cooling.

Tissue may be exposed to radiant energy during or following application of a device of the disclosure. For example, while contacting the tissue, radiant energy may be delivered through one or more pins or between pins. Cooling may be performed during radiant exposure for the purpose of removal of heat from the tissue or through the pin.

Alternatively, in some embodiments, tissue may be exposed to light after release of the vacuum and the device has been removed, but before the site has resumed its original state. Generally, methods and devices of the disclosure may be used in any tissue. For example, methods and devices, according to some embodiments, may be used with any tissue or organ covered by dermis or epidermis. In some embodiments, tissue may be visualized through a layer of mucosa.

Eight different example devices were manufactured with the specifications listed in Table 4.

TABLE 4

Example device specifications

| | Device Number | | | | | | | |
|---|---|---|---|---|---|---|---|---|
| | 1 | 2 | 3 | 4 | 5 | 6 | 7 | 8 |
| Pin Diameter [mm] | 1 | 1 | 1 | 1 | 0.5 | 0.5 | 0.5 | 0.5 |
| Packing Density [%] | 20 | 20 | 40 | 40 | 20 | 20 | 40 | 40 |
| Pin Surface: Flat/Curved | F | C | F | C | F | C | F | C |

Similarly, blood flow may be diverted as blood is squeezed out of blood vessels underneath individual pins. Due to the applied vacuum, blood vessel diameter may be increased in the tissue surrounding the pins. This causes pooling and collection of blood in tissue between pins.

Net result of this procedure may be the creation of localized (fractional) optical tissue clearing. In contrast to optical skin clearing with hyper-osmotic chemicals this process may be rapid, occurring, for example, in a matter of a few seconds. An additional advantage may be a controlled re-distribution of water, blood and melanin, which may be specific or non-specific targeted tissue chromophores for many laser based therapeutic applications such as non-ablative skin rejuvenation, photothermal coagulation of hyper-vascular lesions, laser hair removal, adipose contouring, adipose reduction and removal, and tattoo removal. In some embodiments, methods and devices of the disclosure may be configured to be non-invasive. Such embodiments may be highly patient compliant and virtually pain free.

Localized reduction of light scattering under each pin creates channels, through which light may be delivered deeper into the tissue. This effect may be facilitated further by designing the device to include radiant filters. The anterior surface, i.e., the side facing away from the skin, may feature micro-lenses as radiant filters, which help to guide and focus incoming radiation into each pin. Depending on the required light delivery depth the pin surface also may feature different optical lensing properties to allow further focusing or spreading of the light beam exiting the pin. In one embodiment, a sapphire ball lens may be used to form a high thermal conductivity radiant filter.

This allows for numerous degrees of freedom to design and tailor the device to meet specific therapeutic requirements and to optimize the therapeutic outcome based on the delivered light profile and depth. The vacuum pressure may also be varied to accommodate different skin conditions and to control the optical clearing depth.

Since the device allows fluid re-distribution (e.g., blood and water, which collect in the tissue peripheral to the pins), different optical designs may be feasible for the treatment of hyper-vascular lesions. Enlarging blood vessels allows better coagulation of vessels, which otherwise may be too small to absorb sufficient energy. Thus, different designs allow therapeutic treatment in tissue between pins as well as under pins. Micro-lens radiant filters may be placed onto different locations on the device, permitting incident laser light to be directed either into pins or into the area between pins.

The ability to deliver light deeper into tissue alleviates one of the most significant limitations in light-based therapeutic applications. Since the pin geometry results in individual light channels separated by tissue which may not be exposed to laser light, an approach similar to fractional photothermolysis may be achieved.

Tissue may be exposed to light during or following application of a device of the disclosure. For example, while contacting the tissue, light may be delivered through one or more pins or between pins. Alternatively, in some embodiments, tissue may be exposed to light after release of the vacuum and the device has been removed, but before the site has resumed its original state. Generally, methods and devices of the disclosure may be used in any tissue. For example, methods and devices, according to some embodiments, may be used with any tissue or organ covered by dermis or epidermis. In some embodiments, tissue may be visualized through a layer of mucosa.

The present disclosure includes, without limitation, a method and apparatus for modifying optical properties of biological tissue. The device described above incorporates several design features, which may improve (e.g., significantly improve) light delivery into tissues such as skin.

By reducing light scattering and re-distributing major tissue chromophores including water, hemoglobin and melanin this device may significantly improve therapeutic and diagnostic use of laser light. Devices of the disclosure may improve therapeutic applications such as laser hair removal, skin rejuvenation and photothermal coagulation of hyper-vascular lesions and non-ablative skin rejuvenation.

Potential applications include but are not limited to, laser hair removal, laser tattoo removal, photothermal coagulation of hyper-vascular lesions, and non-ablative skin rejuvenation, adipose recontouring, adipose reduction, and adipose removal.

Fractional Cooling

There may be conditions under which irradiation of tissue is correlated with adverse and/or unwanted events including, for example, undesirable tissue heating and/or photothermal damage to deeper tissue layers. Accordingly, in some embodiments of the disclosure, a system, device, and/or method of the disclosure may include measures to offset, reduce, and/or eliminate such adverse and/or unwanted events. For example, a system, device, and/or method of the disclosure may include means for fractionally cooling tissue. A fractional cooling device may include, for example, a base (e.g., a planar or substantially base) and a brim contiguous with or fixed to one side of the base, wherein the base and the brim at least partially define a flow chamber. At least a portion of the flow chamber may be defined by the surface of the tissue with which it is contacted.

A thermally-controlled composition (e.g., fluid) may flow through a closed flow chamber (e.g., a flow chamber in contact with skin), for example, via an inlet port and outlet port. The inlet and outlet ports may be positioned anywhere relative to each other. For example, in some embodiments, the inlet and outlet ports may be positioned from adjacent to each other to as far apart as possible.

Figure 4A:
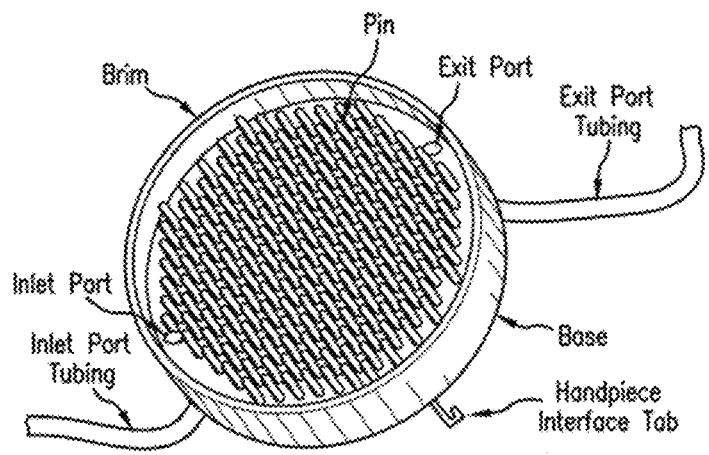
FIG. 4A illustrates an example embodiment of an optical clearing device.
Figure 4B:
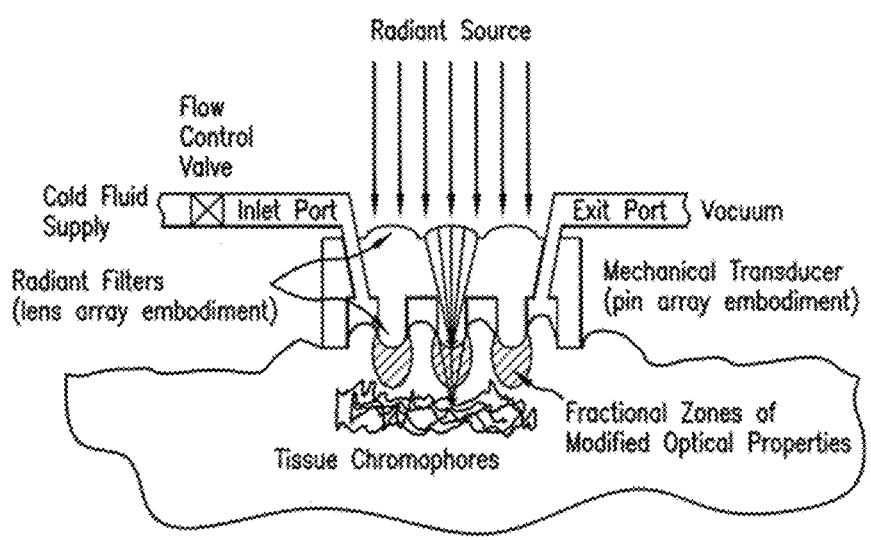
FIG. 4B illustrates an example embodiment of an optical clearing device appressed to a tissue, wherein radiant energy passes through two radiant filters.
Figure 4C:
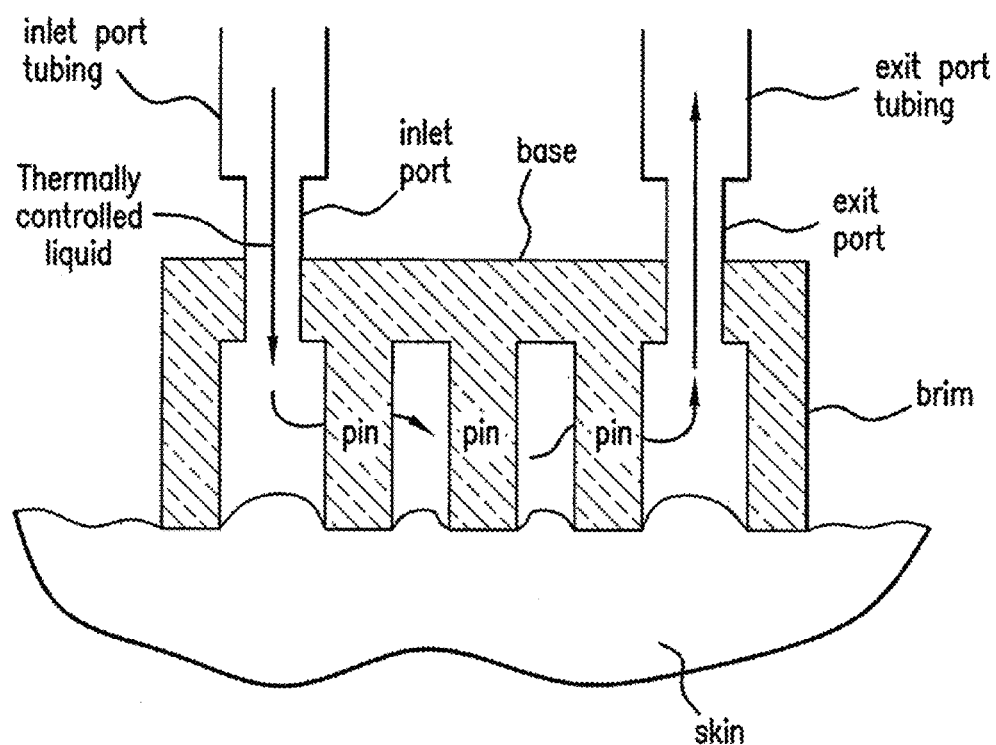
FIG. 4C illustrates an example embodiment of an optical clearing device with cooling, wherein the device is appressed to a tissue and a thermally-controlled fluid is flowing through the flow chamber, which is defined by the base, brim, and appressed skin.

In some embodiments, an optical clearing device may include a flow chamber for fractional cooling. In some embodiments, fractional cooling may include contacting at least a portion of the tissue that will be, is being, and/or was irradiated with a thermally-controlled fluid. This may include, for example, contacting a tissue with an optical clearing device having an inlet and an outlet for a thermally-controlled composition and flowing the thermally-controlled fluid through the inlet and outlet ports such that it contacts at least a portion of the tissue as shown in FIG. 4C.

Nonlimiting examples of a thermally-controlled fluid may include a gas (e.g., nitrogen, oxygen), a mixture of gases (e.g., air) or a liquid (e.g., water). In some embodiments of the disclosure, a thermally-controlled fluid may be purified (e.g., filtered, sanitized, sterilized, or otherwise treated to remove or destroy materials) before and/or after contacting tissue. For example, where the tissue may be sensitive to infection, a thermally-controlled fluid may be pre-sterilized. In another example, a thermally-controlled fluid may be post-sterilized (e.g., filter-sterilized, chemically-sterilized, and/or autoclaved) after contact with a tissue having or potentially having contagions or other biohazardous components. A thermally-controlled fluid may be processed to add or remove water (e.g., vapor) prior to contacting tissue in some embodiments. For example, it may be desirable to humidify air to reduce the potential for tissue dehydration. Alternatively, it may be desirable to dehumidify air to reduce the possibility of contacting tissue with a microbe or other unwanted material or fouling of other system or device components. A fluid may be dehumidified using water removal filters and/or desiccant driers.

The temperature of a thermally-controlled fluid may be regulated using any structures, devices, and/or methods available. For example, the temperature of a thermally-controlled fluid may be regulated using a heat pump or a Ranque-Hilsch vortex tube. Dehumidification may be desired in some embodiments to prevent heat pump or vortex malfunction. In a specific example embodiment, a thermally-controlled fluid may be water that is pre-chilled in an ice-water bath.

In some embodiments, a system or device of the disclosure may include a thermally-controlled fluid and a thermal regulator that controls the temperature of the thermally-controlled fluid. A thermal regulator may include a thermal sensor, a thermostat, and/or a refrigerant. A thermally-controlled fluid may be maintained at a constant temperature or a substantially constant temperature (e.g., ±1° C., ±2° C., ±5° C.), according to some embodiments. In other embodiments, the temperature of a thermally-controlled fluid may ramp, oscillate, or otherwise vary in a regular or irregular manner as the tissue is illuminated. Increasing the velocity and/or turbulence of a thermally-controlled fluid may escalate heat loss from tissue. Tissue heat removal may be additionally aided by minimizing the chamber volume and using internal chamber features, such as a pinned surface, which disrupt laminar flow.

In some embodiments a system or device of the disclosure may include thermal sensors configured and arranged to monitor, for example, the temperature of at least a portion of (a) a tissue at or near a site of illumination, (b) an optical clearing device, and/or (c) a thermally-controlled fluid. A thermal sensor or combination of thermal sensors may also be configured and arranged to monitor, for example, a temperature difference between at least a portion of (a) a tissue at or near a site of illumination, (b) an optical clearing device, and/or (c) a thermally-controlled fluid.

A device or system of the disclosure may include, in some embodiments, a vacuum pump in fluid communication with and located downstream of an exit valve. The action of a vacuum pump may seal the device against a tissue surface and/or actuate or enhance fluid flow. A device or system of the disclosure may include, in some embodiments, one or more valves (e.g., a solenoid valve) in fluid communication with an inlet and/or an exit port. A valve may partially or completely regulate thermally-controlled fluid influx and/or efflux from a flow chamber.

Thermal regulation may, according to some embodiments, reduce the temperature of superficial tissue layers prior to or during optical radiation in order to target photothermal change in deeper tissue layers. In addition, systems, methods, and devices may include thermal regulation for lateral spatial control of heat flux out of tissue. For example, heat flux out of irradiated tissue regions may be different from regions where laser irradiation does not enter. In some cases, cooling following radiant exposure may be performed.

According to some embodiments, a method of the disclosure may include administering an optical treatment or therapy. Non-limiting examples of optical treatment or therapy may include blood vessel coagulation, hair removal, wrinkle removal, adipose recontouring, adipose reduction, and adipose removal (fat removal), and melanoma hyperthermia.

Skin and pins may be cooled convectively and/or evaporatively due to the cold substance injected within the chamber. Pins may comprise an optically transparent high thermal conductivity material including plastic, glass, sapphire and/or diamond. Sides of pins may be coated, according to some embodiments, with an opaque high thermal conductivity material (e.g. copper). This coating may further enhance heat flux from skin to convective fluid.

Figure 4D:
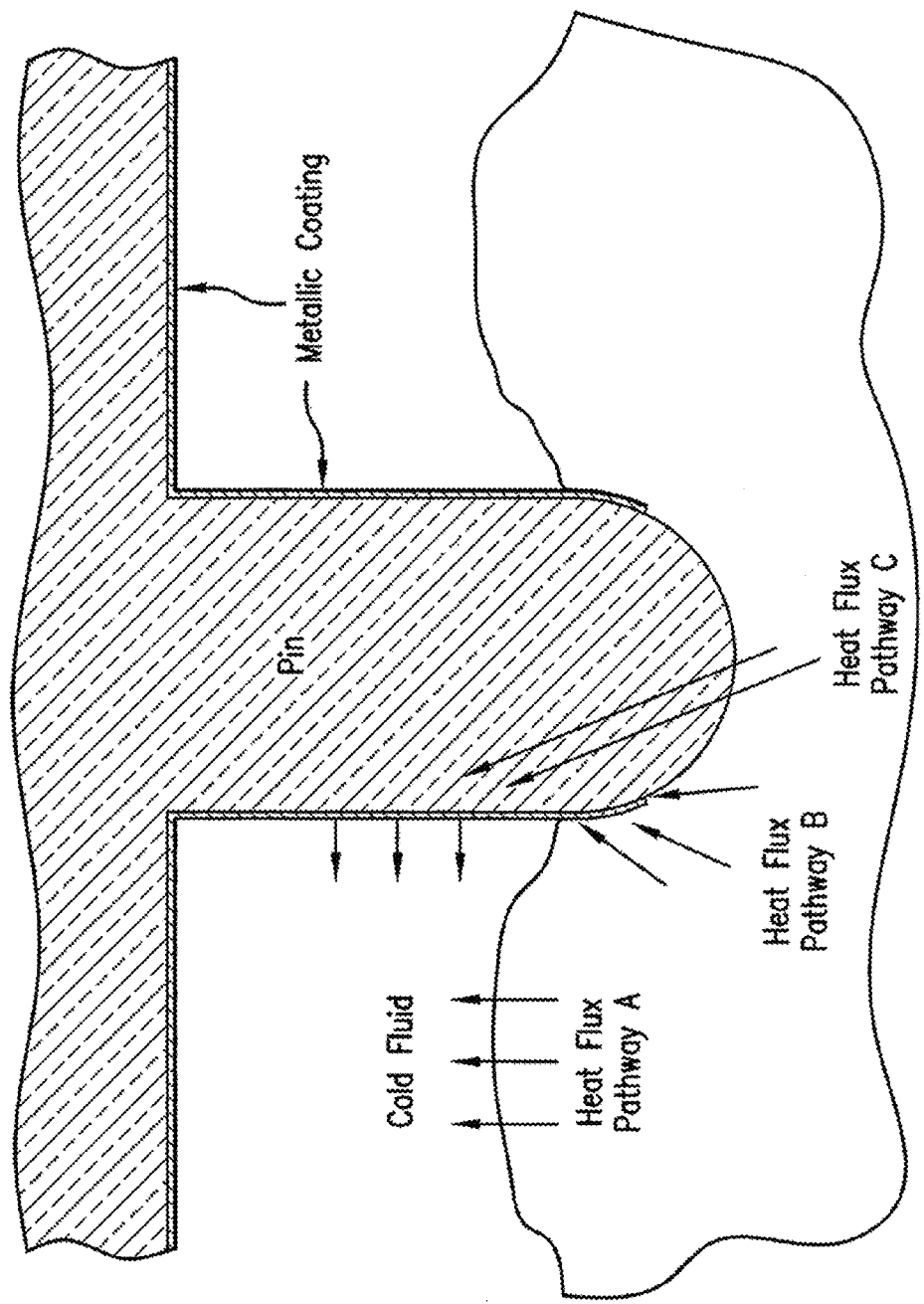
FIG. 4D illustrates an example embodiment of a pin of an optical clearing device contacting skin that is being irradiated, wherein the skin may transfer heat to a thermally-controlled fluid by one or more of the indicated pathways.

As shown in FIG. 4D, a fractional cooling system may be configured and arranged to have one or more heat flux pathways. For example, heat may be transferred by conduction through skin and/or convection from a skin surface to a thermally-controlled fluid (e.g., a cold fluid) (Heat Flux Pathway A). Also, heat may be transferred by conduction through skin, conduction through a metallic pin coating, and/or convection from a metallic pin coating to a thermally-controlled fluid (e.g., a cold fluid) (Heat Flux Pathway B). Heat may be transferred by conduction through skin, conduction through a pin, conduction through a metallic pin coating, and/or convection from metallic pin coating to a thermally-controlled fluid (e.g., a cold fluid) (Heat Flux Pathway C). Components of an optical clearing device may be configured and arranged (e.g., by adjusting the pin coating and/or diameter) to strike a desired balance between these pathways. In some embodiments, the balance may include portions of all three pathways while in others one or two of these three pathways may be substantially or completely excluded.

Figure 4E:
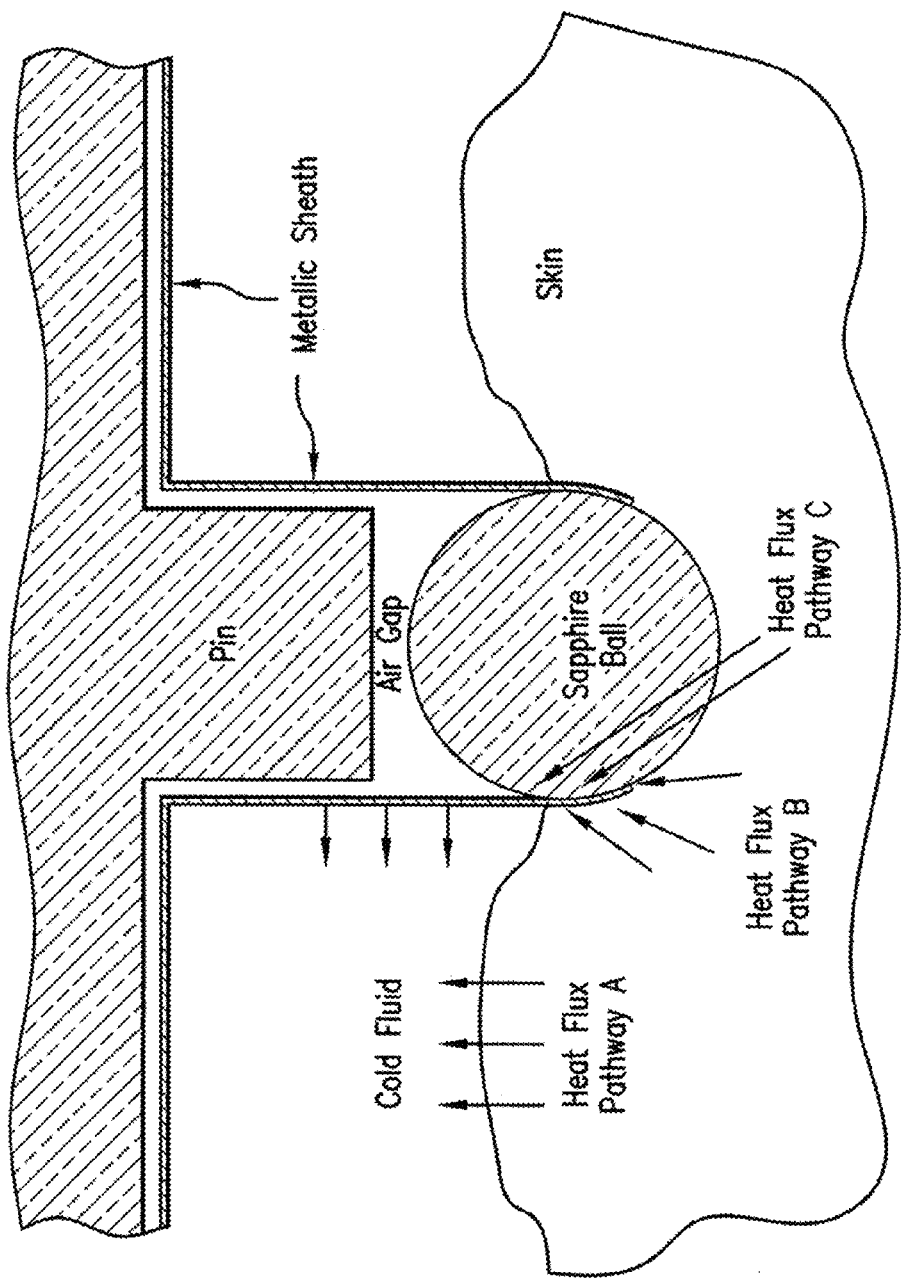
FIG. 4E illustrates an example embodiment of an optical clearing device with a fractional cooling system with a sapphire ball lens, wherein the skin may transfer heat to a thermally-controlled fluid by one or more of the indicated pathways.

As shown in FIG. 4E, a sapphire ball lens, according to some embodiments, may be positioned at the pin tip and a highly conductive (e.g., metal) tube or sheath is placed around the pin with an air-space between the pin and inner surface of the tube. The sapphire ball lens is thermally connected to the highly conductive tube so that thermal energy in the tissue can be conducted into the ball lens, though the highly conductive tube and dissipated with the thermally-controlled fluid.

Systems, devices, and methods according to some embodiments, may include a feedback mechanism. For example, a feedback mechanism may include activating or deactivating a radiant source when a temperature reaches a threshold value. In some embodiments, tissue may be pre-cooled and a feedback mechanism may trigger a radiant source once the tissue temperature has been lowered by a pre-set desired value (e.g., 30° C.). In some embodiments, a feedback mechanism may be configured to shut down a radiant source if the temperature of a tissue exceeds a pre-set value (e.g., 40° C.).

Without limiting any particular embodiment of the disclosure, fractional cooling may provide one or more of the following benefits: tissue alignment with radiant source, efficacy, controllability, repeatability, and uniformity of tissue temperature profile, treatment procedure safety, and environmental sensitivity. In addition, formation of the chamber may be useful in that stabilizing the tissue surface against the chamber allows alignment of the tissue perpendicular to the radiant source. In some embodiments, an optical clearing device may include a pinned chamber surface that increases the surface area of skin in contact with cold fluid and increases turbulence of the fluid stream, which may increase heat flux from the tissue surface. Controllability of the technique and device may be enhanced by fine regulation of the fluid flow rate, temperature, and flow duration in the environmentally isolated chamber. Repeatability and uniformity of temperature profile of skin may be enhanced at least in part because the chamber is isolated from exterior environmental conditions and flow is uniform across the chamber surface. Treatment procedure safety may be enhanced due to tissue alignment with radiant source and enhanced efficacy, controllability, repeatability, and uniformity of tissue temperature profile, and temperature feedback device.

A thermally-controlled fluid may include one or more gasses such as nitrogen, oxygen, and air. A gaseous thermally-controlled fluid may be cooled using a vortex tube. Although systems, devices, and/or methods of the disclosure may include materials like R-12 and R-134a in some embodiments, cooling a thermally-controlled fluid with a vortex tube, may, in some embodiments, reduce or obviate the use of these or other such materials.

Wearable Systems and Devices

In some embodiments of the disclosure, a tissue such as skin or adipose, may be treated with optical radiation from an array of light emitting diodes (LEDs). Contacting a tissue with LED radiation may effect a photo-induced change in a targeted tissue region. Conditions that may be treated with LED radiation may include hair removal, wrinkle removal, and fat removal or shaping. A system, device, and method of the disclosure may be used independently or in conjunction with other treatment modalities such as ultrasound, radiofrequency (RF), or optical.

Figure 5:
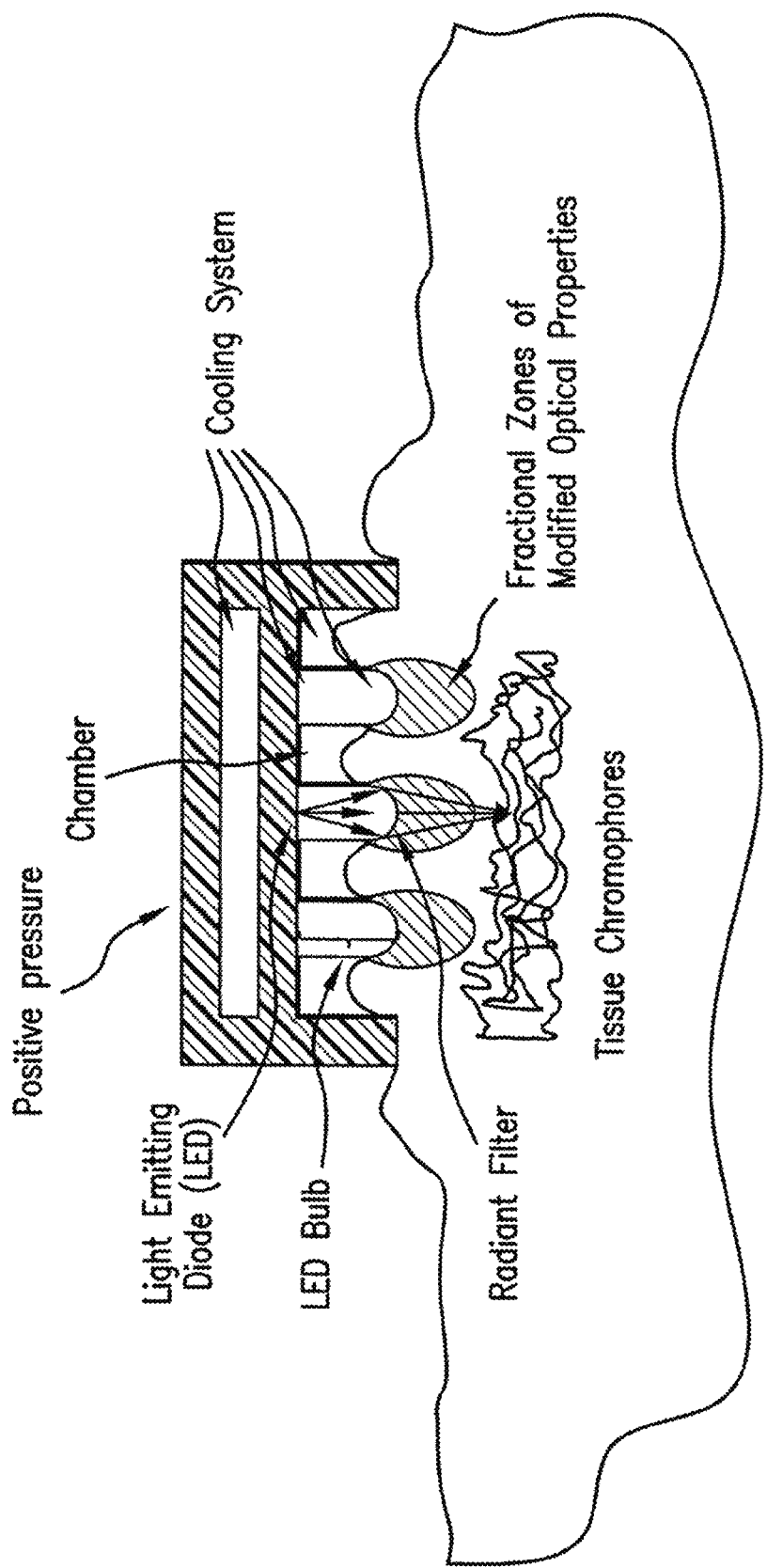
FIG. 5 illustrates a structural embodiment of a treatment device comprised of an array of light emitting diodes, which may be positioned against the skin, resulting in the formation of a closed chamber between the LED array and skin.

A device may be structurally embodied as an array of LEDs which may be positioned against the skin, resulting in the formation of a closed chamber between the LED array and skin. See FIG. 5. LEDs may function as a source of radiant energy, radiant filters (LED bulb), and may integrate tissue optical clearing and cooling technologies into a single device.

A system, device, or method of the disclosure may be suited for integration with a mechanical tissue clearing device. Application of mechanical forces to the tissue may provide at least three important functions: first, intracellular and interstitial water may be moved out of a targeted tissue volume causing spatial distribution of scatterers to be modified and thereby reduce light scattering and water absorption; second, application of mechanical forces may increase or decrease blood volume fraction and perfusion in selected tissue regions; and third, application of mechanical forces may increase or decrease the tissue volume or thickness. In this embodiment, a material surface enclosing each LED or bulb may also function as a mechanical transducer or pin. An array of LEDs with bulbs may comprise a pin array in contact with the tissue. The LED bulbs may be forced against skin using negative gas pressure in the chamber, positive gas pressure in the form of an inflatable cuff placed behind the LED array, an elastomeric material, gravity, or combinations thereof.

A system, device, or method of the disclosure may be suited for integration with a tissue cooling device. Tissue cooling may reduce the temperature of superficial tissue layers prior to or during optical radiation in order to target photo-induced change in deeper tissue layers Skin may be cooled directly by spraying cryogen or chilled fluid within the chamber. Alternatively, skin may be cooled indirectly by reducing the temperature of an LED bulb array. An array of LED bulbs may be convectively cooled by spraying cryogen or chilled fluid either on the back surface of the LED array or within each LED bulb. See FIG. 5. The bulb covering each LED may be constructed entirely of an optically transparent high thermal conductivity material such as sapphire. Alternatively, sidewalls of LED bulbs may be constructed of an opaque high thermal conductivity metal (e.g., copper). In a different embodiment, skin may be cooled using convectively cooled tubing placed beneath the LED bulbs. Tubing may additionally function to optically clear the skin by mechanically transducing the forces acting on the LED bulbs as illustrated by the right-most pin shown in FIG. 5.

Without limiting any particular embodiment of the disclosure, a system, device, or method of the disclosure may provide one or more of the following benefits: cost reduction, ease of patient/operator use, and treatment procedure efficacy, repeatability, and safety. Replacement of a conventional laser source with an LED array provides reduction in cost and ease of operation. Simplicity of device operation may permit use in different environments because the device may operate without sophisticated controls, operator expertise, and implementation facilities, thereby reducing operational costs. Efficacy and repeatability of the treatment procedure may be enhanced by integrating tissue clearing and tissue cooling technologies with an environmentally isolated chamber. Repeatability of skin temperature profile may be enhanced because the chamber is isolated from exterior environmental conditions. Uniformity of skin temperature may be enhanced by regular spacing of LED array elements which provide consistent subsurface heating and superficial cooling. In some applications, safety of the procedure may be enhanced by utilizing a low-power steady-state heat transfer regime in contrast to conventional high-power transient regimen of laser therapeutic techniques.

According to some embodiments of the disclosure, an optical clearing device may optionally include a tissue cooling feature and/or may be configured and arranged into a single, wearable device. A wearable system or device of the disclosure may be suitable for in-home therapy or use. In some embodiments, a wearable system or device may be used for therapeutic procedures such as hair removal, wrinkle removal, and fat removal or shaping. A system, device, and method of the disclosure may provide a non-invasive alternative to existing invasive surgical procedures.

thickness may be important in application of RF energy to selected chromophores such as cellulite.

Application of RF energy in conjunction with the tissue clearing device may be integrated functionally and structurally with tissue clearing/tissue cooling methods, systems, and devices to aid RF tissue therapy. The integrated technique/device optically clears and cools superficial layers of tissue (e.g., skin) therefore protecting it from thermal damage during therapeutic RF and/or light treatments. In addition the tissue clearing/cooling device may be configured to provide dynamic cooling of RF electrodes that are integrated into the device.

The functional/structural synergism of an RF tissue treatment application is described below and illustrated in Table 5. According to some embodiments, a system or device of the disclosure may displace water (an RF chromophore) and remove heat from the superficial layers of the tissue. This may enhance an RF procedure by reducing chromophore (water) density and initial temperature of non-target (superficial) tissue thus constraining thermal damage to targeted (deeper) tissue such as reticular dermis or adipose. If a combined RF/optical treatment is desirable, optical properties of superficial tissue may be modified, potentially allowing more light (fluence) to reach target chromophores.

TABLE 5

Functional/structural synergism of an RF tissue treatment application.

| Functional Elements | Potential Structure | | | | |
|---|---|---|---|---|---|
| Radiant Source | Laser | Radio Frequency | Microwave | X-ray | LED |
| Mechanical Transducer | Chamber | Pins | Vacuum | RF probe | |
| Radiant Filters | Mask (e.g., RF probe) | Lenses | | | |
| Cooling | Chamber | Pins | RF probe | Convective fluid | Evaporative Liquid |
| Feedback | Optical Feedback | Temperature feedback | Mechanical Feedback | Electrical Feedback | Ultrasonic feedback |
| Tissue Position and Hold | Chamber | Pins | Vacuum | RF probe | |
| Tissue and Chromophores | Melanin | Hemoglobin | Water | Dye | |

Radio Frequency Sources

According to some embodiments of the disclosure, a system, device, and method may include contacting a tissue with a radio frequency energy. For example, a tissue clearing device may include a radio frequency source. A radio frequency source may be combined with tissue cooling and/or laser irradiation. Without limiting any particular embodiment, a tissue clearing system, device, or method that includes a radio frequency source ("an RF tissue clearing device") may be used in connection with cellulite treatment, acne vulgaris treatment, and wrinkle removal.

Application of a mechanical force in association with radio frequency (RF) exposure may provide one or more of the following. First, intracellular and interstitial water may be moved out of a targeted tissue volume causing spatial distribution of scattering particles to be modified and thereby reduce light scattering and reducing absorption of RF energy in these areas. Second, application of mechanical forces may increase or decrease blood volume fraction and perfusion and modulate tissue's natural response to maintain hydration. Third, application of mechanical forces may increase or decrease the tissue volume or thickness. Modifying tissue RF probes may provide many benefits to the other functional elements of the system. For example, RF probes may contribute in full or part to the radiant energy provided to the tissue. Secondly, RF probes may contribute in full or part to the mechanical transduction function of the system. Mono or bi-polar RF probes may be structurally embodied within the chamber of the device and may serve to compress or stretch tissue, locally modifying tissue chemical content (e.g., hydration) and therefore optical/thermal properties. Third, RF probes may contribute in full or part to filtering optical radiant energy. For example, RF probes placed on the base of the chamber device may block (mask) optical radiant energy from reaching tissue, and RF probes placed along the sides of pins may guide (reflect) optical radiant energy toward pin tips. Fourth, RF probes placed along the sides or near pin tips may enhance cooling functionality of the device since metal RF probes are excellent heat conductors. Fifth, RF probes may serve additional functionality as temperature or electrical resistance feedback probes utilizing the excellent heat and electrical conductance properties of metal. Finally, RF probes may serve to position and hold tissue prior to and during treatment in the same manner as pins.

EXAMPLES

The results presented in the following may be obtained with some of the 8 different example devices. The devices differ with respect to their pin size, packing density and pin surface, which was either flat or curved. Refer to Table 4 for device specifications.

Example 1

Observations on Human Skin

The device was applied to the bottom of the lower arm and pressed into the skin. Observations may be possible through the applied device and after device removal.

Pressing the device onto the skin without vacuum caused some reddening of the tissue surrounding the pins. This was caused by the displacement of blood from underneath the pins. Skin under the pins turned pale in appearance. After removal of the device the previously described skin color changes persisted for several seconds before pale, blood-voided skin slowly became more red and the increased red appearance of peripheral tissue decreased.

Figure 7A:
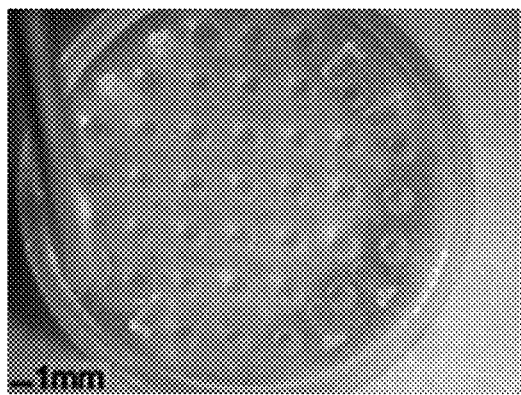
FIG. 7A is a photograph showing redistribution of blood and interstitial water in human skin following application of Example Device No. 2.
Figure 7B:
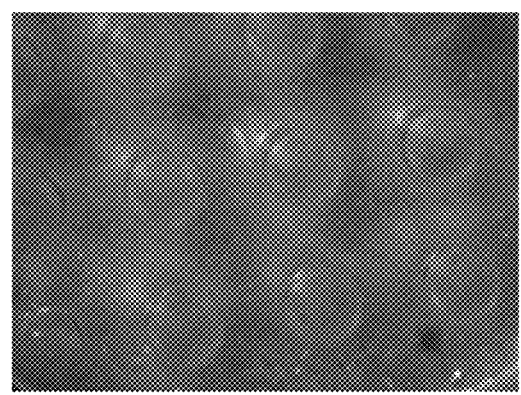
FIG. 7B is a photograph showing redistribution of blood and interstitial water in human skin following application of Example Device No. 2

Applying a vacuum of ~750 mm Hg added significantly to the benefits of the device. The mechanical stress on the tissue underneath the pins was noticeably increased, resulting in better stretch and more complete conformation of the skin around each pin. This added mechanical influence caused more complete displacement of interstitial tissue water and blood. This may be seen in FIGS. 7(a) and (b). These images as well as FIGS. 8(a) and (b) may be acquired using crossed polarizers to eliminate spurious surface reflections.

Within seconds, the tissue surrounding the pins turned more white in appearance. This may have been caused by either decreased hemoglobin concentration or increased light scattering due to the higher water content of skin similar to the effect known from prolonged bathing or dish washing, which also result in super-hydration of skin. Another side effect was an immediate reddish hue of the skin as a result of increased blood pooling. This effect was much more pronounced with the vacuum applied, since the low pressure increased the blood carrying capacity by dilating the blood vessels.

Upon removal of the device, skin underneath pins appeared with a slightly bluish tint, indicative of reduced light scattering of the longer or red visible wavelengths.

Figure 8A:
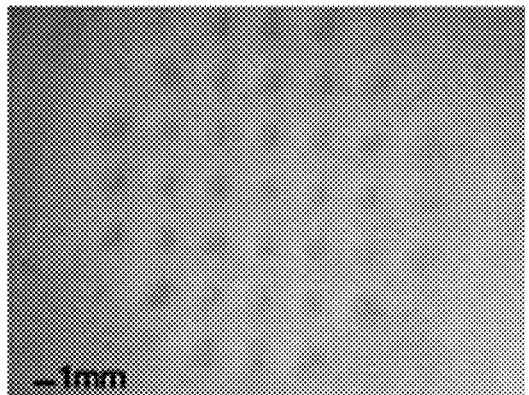
FIG. 8A is a photograph showing in vivo human skin following application and removal of Example Device No. 2.
Figure 8B:
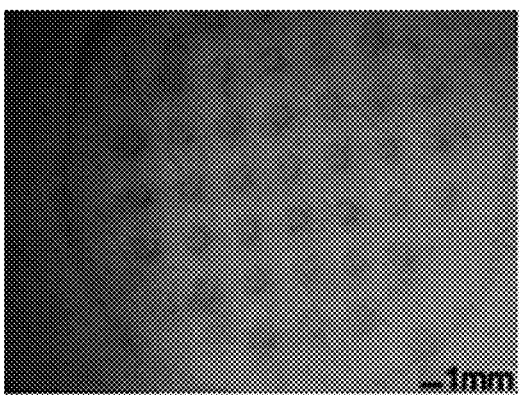
FIG. 8B is a photograph showing in vivo human skin following application and removal of Example Device No. 2

Within seconds of device removal, normal blood flow re-established causing the optically cleared skin to appear bright red. Skin indentations persisted for several minutes. During this time, also the white appearance of the pin peripheral tissue disappeared as it was reperfused. These results are shown in FIGS. 8(a) and (b). Inhomogeneities in skin appearance may be due to locally altered tissue optical properties.

Example 2

Unaided Eye Observations on In Vitro Pig Skin

Figure 9A:
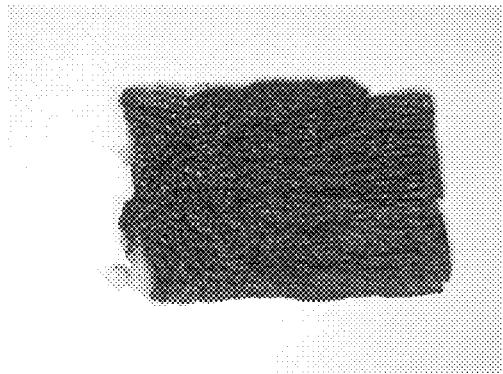
FIG. 9A is a bright-field photograph illustrating an epidermal view of in vitro porcine skin following application and removal of Example Device No. 1.
Figure 9B:
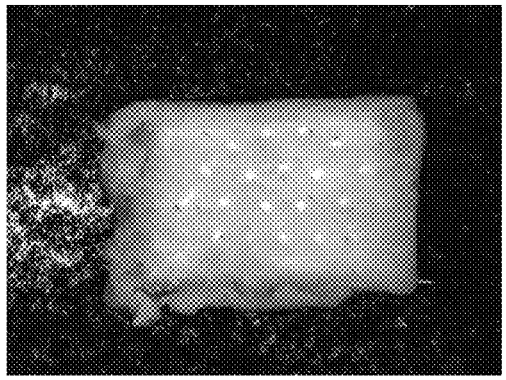
FIG. 9B is a transmission photograph illustrating a dermal view of in vitro porcine skin after Example Device No. 1 has been removed.

The advantage of using in vitro tissue may be the ability to observe transmitted light through the specimen. Porcine skin may be comparable to human skin and was used for this experiment. The sample was previously snap frozen in liquid nitrogen and allowed to thaw at 25° C. The epidermis was highly pigmented and therefore significantly attenuated visible light transmission, cf. FIGS. 9(a) and (b).

However, as the Example Device No. 1 was applied to the skin, locally increased light transmission was immediately apparent. Removal of the device from the skin after a few seconds allowed direct visualization of locally increased light transport through the tissue, which was compressed and mechanically dehydrated by the pins.

Figure 10A:
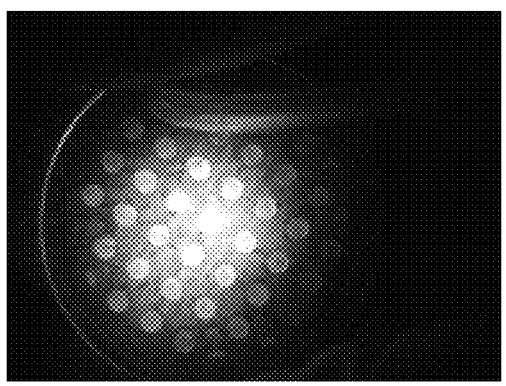
FIG. 10A is a photograph illustrating in vitro porcine skin subjected to broadband continuous-wave white light transmitted through skin and Example Device No. 1.

Similarly, digital photographs may be acquired using in vitro porcine skin while device no. 1 was applied to the skin surface. Light from a broadband CW white light source was transmitted through the tissue. FIG. 10(a) shows transmission of white light through an approximately 2 mm thick in vitro pig skin sample. The Example Device No. 1 was applied to the skin surface and the significant change of optical tissue properties may be evident from the increased light transport through the tissue which may be locally optically cleared by the pins. Notice also the lower spectral filtering, making transmitted light appear white, whereas in tissue regions surrounding the pins, selective wavelengths may be filtered due to absorption or scattering in the skin sample.

Figure 10B:
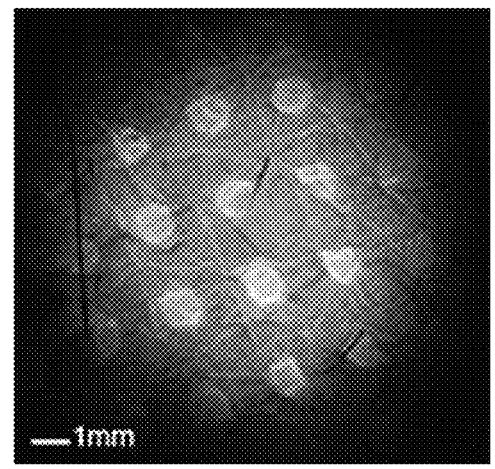
FIG. 10B is a photograph illustrating in vitro porcine skin subjected to broadband continuous-wave white light transmitted through skin after Example Device No. 1 has been removed.

FIG. 10(b) shows the same tissue specimen after the device was removed from the skin surface. The locally enhanced transmitted light intensity may be evident again, although the overall intensity seems slightly reduced. This observation, in spite of identical experimental conditions supports the claim, that devices of the present disclosure facilitate better light delivery into deep skin layers. Here, pins may be used to better view transmitted light through skin, but the same increased light transport may be observed when light is delivered through the pins.

Figure 11:
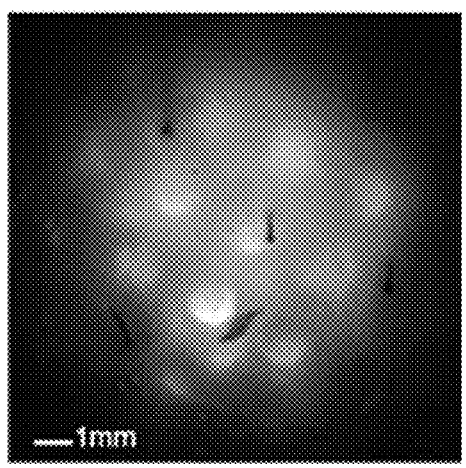
FIG. 11 is a photograph illustrating a dermal view of porcine skin shown in FIG. 10B.

FIG. 11 shows the dermal view of the same skin sample shown in FIG. 10(b). Although the optical clearing device was removed from the skin sample, locally increased light transmission may still be observed. This image also shows some hair follicles. Particularly for laser hair removal the therapeutic outcome strongly depends on the ability to deliver light deep into skin.

Example 3

Optical Coherence Tomography Measurements at 1290 nm on In Vivo Human Skin

Optical coherence tomography as a non-invasive imaging modality may be a very useful tool in assessing not only skin deformation and compression due to the device but also to analyze improved light transport within the compressed tissue. Acquisition of lateral cross-sectional images of tissue permitted observation of the contrasting light propagation in tissue underneath pins and between pins. The following OCT images may be acquired on the lower arm of human subjects.

Figures 12A, 12B:
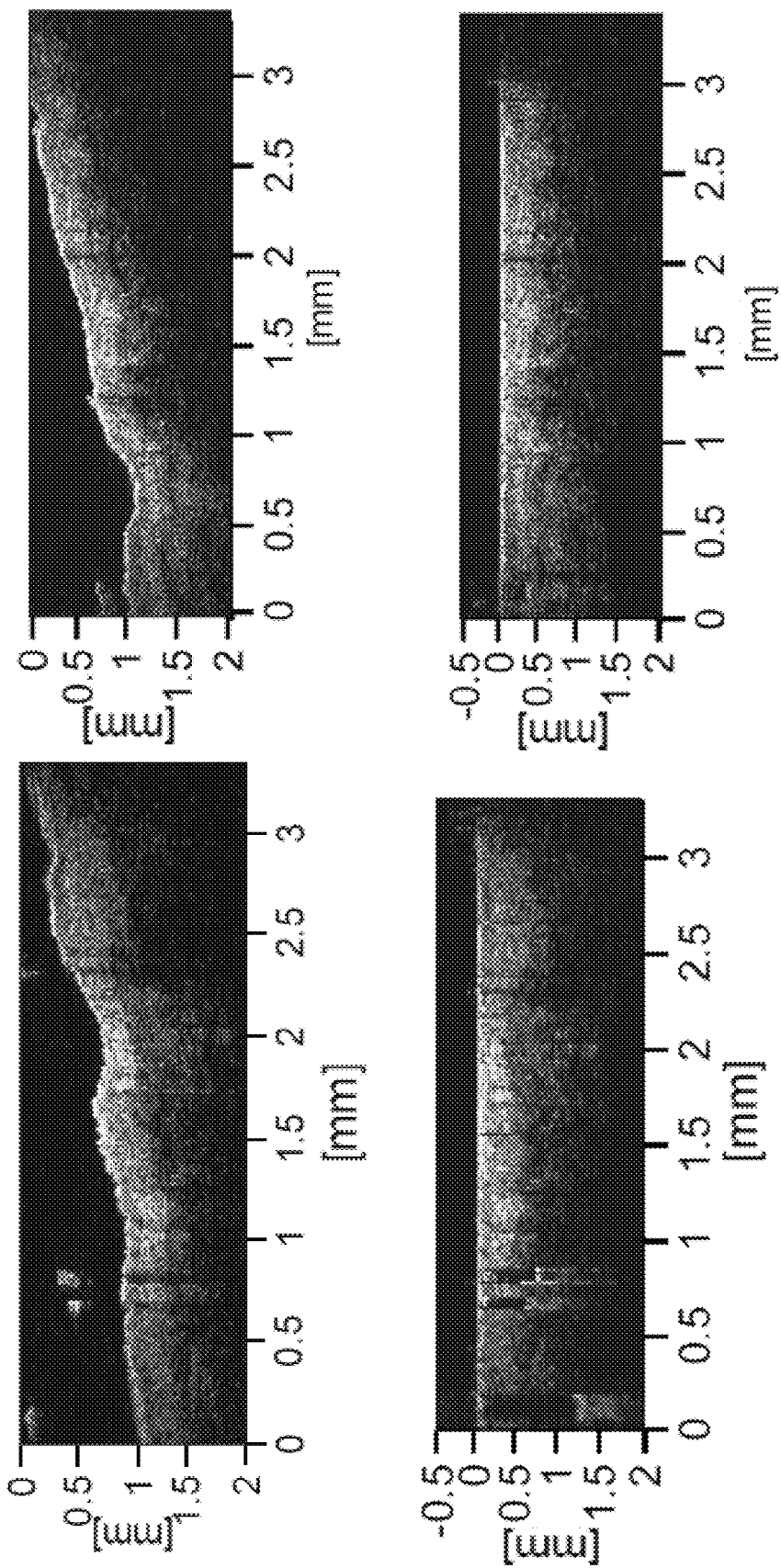
FIG. 12A is an OCT image at 1290 nm wavelength illustrating effects of the application of Example Device No. 3 to in vivo human skin on the top surface of the lower arm, wherein the device has been removed. The upper portion of the figure is the original image which has been digitally processed to re-register the tissue surface to a common flat level as shown in the lower portion of the figure.
FIG. 12B is an OCT image at 1290 nm wavelength illustrating effects of the application of Example Device No. 3 to in vivo human skin on the bottom surface of the lower arm, wherein the device has been removed. The upper portion of the figure is the original image which has been digitally processed to re-register the tissue surface to a common flat level as shown in the lower portion of the figure.

For easier comparison of the OCT imaging depth the original image shown on the top of each figure was digitally processed in order to re-register the tissue surface to a common flat level shown in the bottom part of each figure. OCT images in FIGS. 12(a) and (b) may be acquired with device no. 3 and nicely illustrate the enhanced light penetration depth in areas of previously compressed tissue. The image in FIG. 12(a) was obtained from the top surface of the lower arm and there may be hair visible above the tissue surface. FIG. 12(b) was obtained from the bottom arm surface.

Figures 13A, 13B:
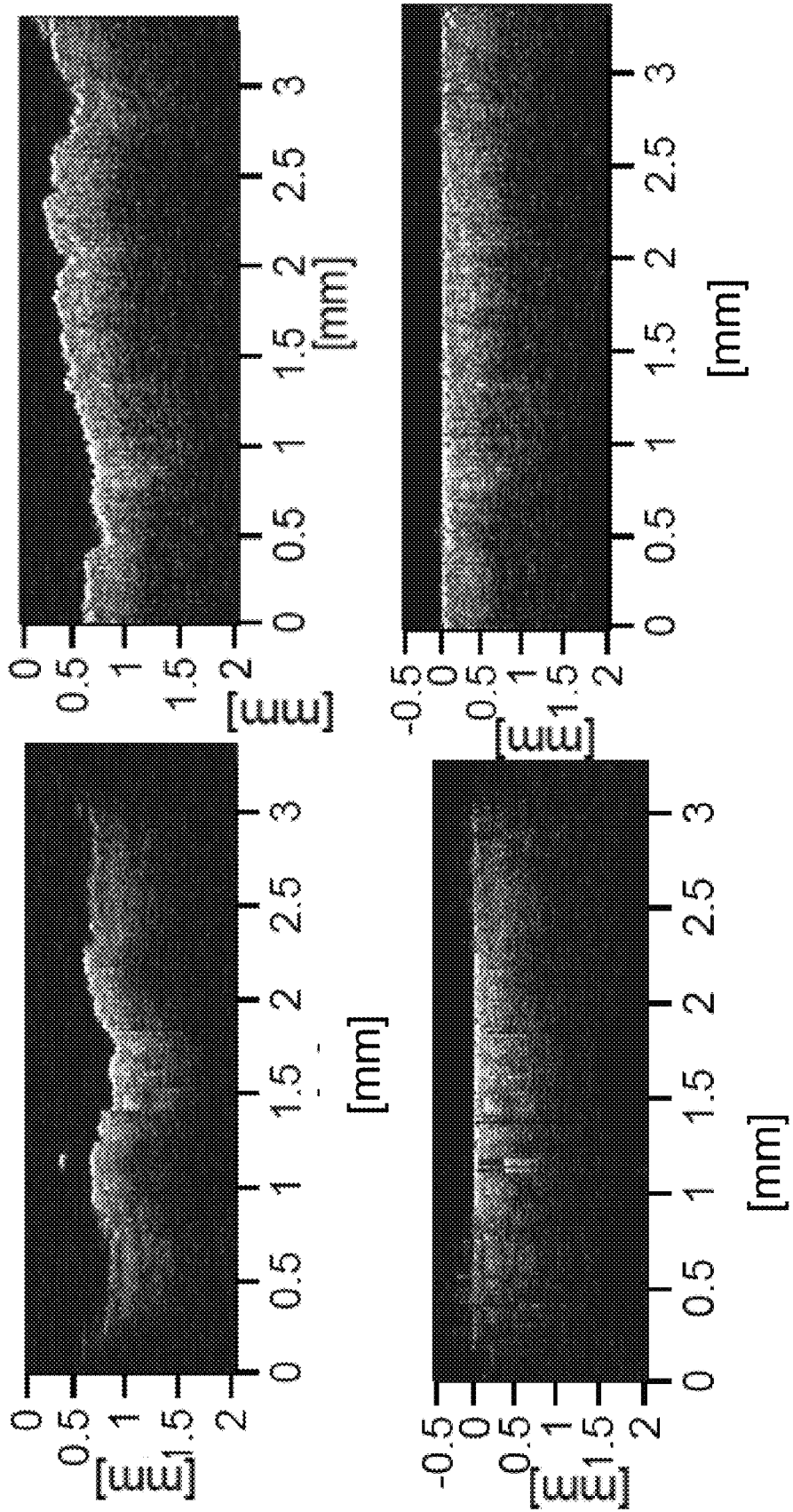
FIG. 13A is an OCT image at 1290 nm wavelength illustrating effects of the application of Example Device No. 1 to in vivo human skin on the top surface of the lower arm, wherein the device has been removed. The upper portion of the figure is the original image which has been digitally processed to re-register the tissue surface to a common flat level as shown in the lower portion of the figure.
FIG. 13B is an OCT image at 1290 nm wavelength illustrating effects of the application of Example Device No. 1 to in vivo human skin on the bottom surface of the lower arm, wherein the device has been removed. The upper portion of the figure is the original image which has been digitally processed to re-register the tissue surface to a common flat level as shown in the lower portion of the figure.

Similar results may be obtained with device no. 1 after it was removed from the skin. See FIGS. 13(a) and (b). It may be noted that many of these images may be acquired up to several minutes after the device was removed from the skin surface. Since skin dynamically rehydrates, OCT images acquired at later time points show less prominent optical clearing results. Nevertheless, it may be a great advantage that induced tissue clearing persists for a few minutes even after the device was removed from the skin.

Figures 14A, 14B:
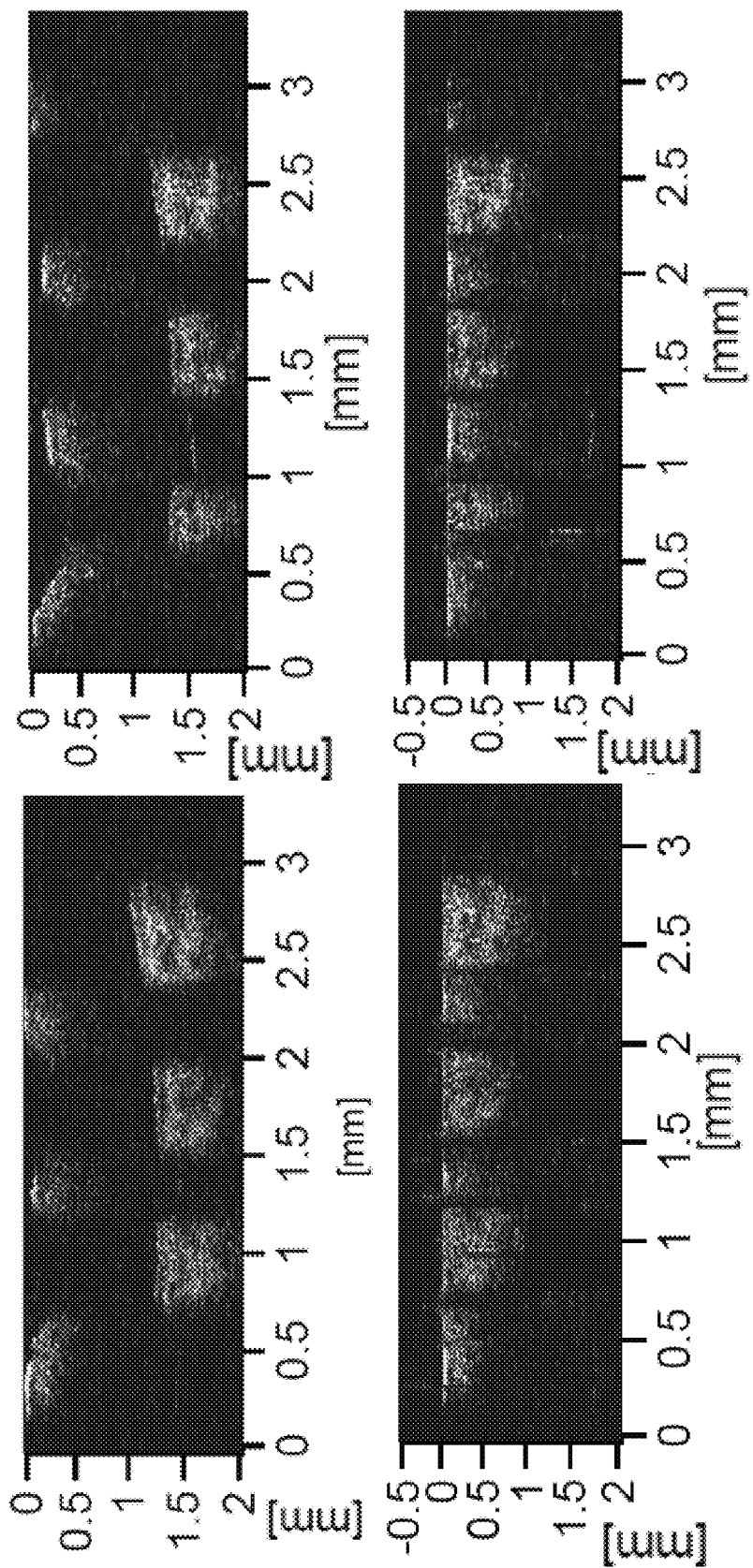
FIG. 14A is an OCT image at 1290 nm wavelength illustrating effects of the application of Example Device No. 1 to human skin on the surface of the lower arm, wherein the device is still applied. The upper portion of the figure is the original image which has been digitally processed to re-register the tissue surface to a common flat level as shown in the lower portion of the figure.
FIG. 14B is an OCT image at 1290 nm wavelength illustrating effects of the application of Example Device No. 1 to human skin on the surface of the lower arm, wherein the device is still applied. The upper portion of the figure is the original image which has been digitally processed to re-register the tissue surface to a common flat level as shown in the lower portion of the figure.

Images shown in FIGS. 14(a) and (b) were acquired through the device while it was in contact with skin. These images demonstrate embodiments of the disclosure which permit high resolution tissue imaging through the device. Also, skin deformation around the pins may be reduced.

Most importantly, this data proves the claimed benefit of enhanced light transport into the tissue through the pins into local optically cleared channels through which light may propagate through skin into deeper layers. This effect may be illustrated nicely with the re-registered surface data shown in the bottom half of FIGS. 14(a) and (b).

Example 4

Optical Coherence Tomography Measurements at 850 nm on In Vivo Human Skin

Figure 15A:
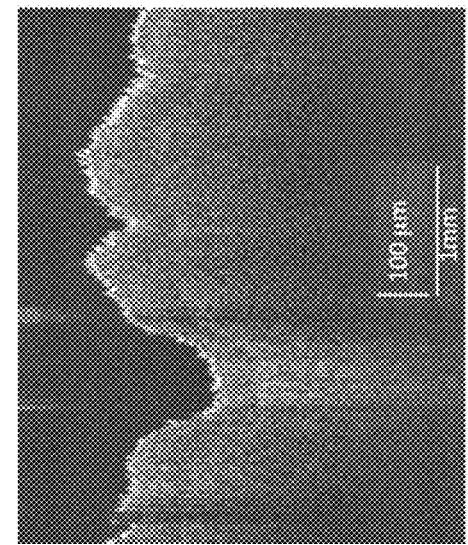
FIG. 15A is an OCT image at 850 nm wavelength illustrating effects of the application of Example Device No. 1 to human skin on the surface of the lower arm, wherein the device has been removed.
Figure 15B:
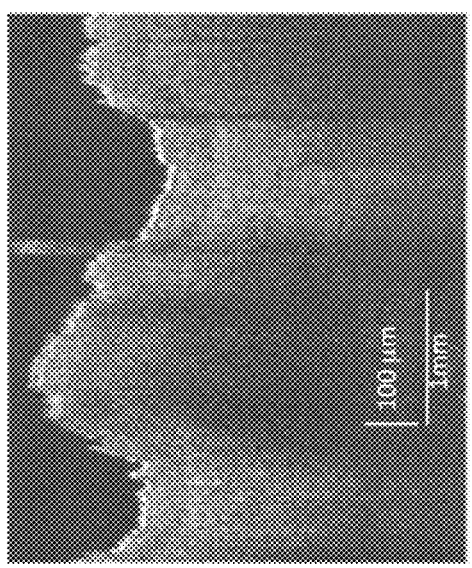
FIG. 15B is an OCT image at 850 nm wavelength illustrating effects of the application of Example Device No. 1 to human skin on the surface of the lower arm, wherein the device has been removed.

FIG. 15 shows in vivo human skin after device no. 1 was removed from the skin surface. Due to the shorter wavelength of this OCT system in contrast to the 1290 nm system, there may be more light scattering. These images therefore show greater contrast between optically cleared and native skin. The images in FIG. 15 illustrate the increased penetration depth of 850 nm light which correlates directly with the indented marks on the skin resulting from the pins. TABLE-US-00006 TABLE 5 Summary of anatomical sites and vacuum condition for OCT M-scans Human Subject No. Anatomical Site Vacuum FIG. NO. I volar forearm good 16(a) II palm of hand good 16(b) III top of hand partial 17(a) III volar forearm good 17(b) III volar wrist good 18(a) III thumb/index good 18(b) finger Example 5

Time-Resolved OCT Images of In Vivo Human Skin at 1310 nm

Using a fast scanning OCT system at a center wavelength of 1310 nm±30 nm permits data acquisition at a considerably faster rate (100 B-scans per second) compared to the previously used time domain OCT systems before. This enabled time-resolved cross sectional OCT images of in vivo human skin. These so called M-scans may be taken over a lateral range of 1 mm through a single pin of Example Device No. 1.

In an M-scan the OCT image evolves around a central line of symmetry where the top part of the image appears as a mirror image of the bottom part. Although not truly a mirror image, top and bottom part of the M-scan may be formed by scanning into and out of the tissue. The images presented in the following figures may be interpreted as a function of time. For each time step, a single OCT image was averaged across the lateral range of 1 mm. These averaged OCT images then form the columns within each complete M-scan corresponding to each point in time.

This graphical representation of OCT data permits direct visualization of the cross-sectional tissue structure and the time-resolved changes of tissue optical properties. Example device 1 may allow more light delivery into deeper tissue layers improving image contrast and making deep tissue layers appear brighter. Table 5 summarizes the tissue sites and vacuum conditions for each of the OCT M-scans presented in the following.

Figure 16A:
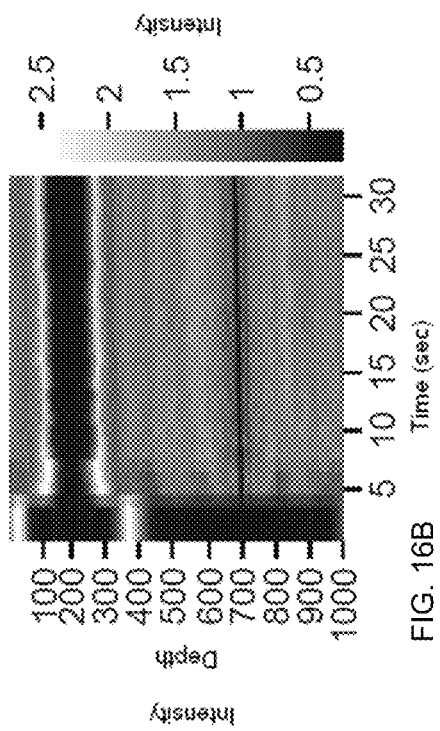
FIG. 16A is an OCT M-scan at 1310 nm wavelength illustrating in vivo human skin on volar forearm of Human Subject No. I which has been brought into contact with Example Device-No. 1 under good vacuum conditions.

FIG. 16 shows M-scans of the volar forearm and palm of the hand of two human subjects. FIG. 16(a) shows the volar forearm of human subject I. The arm was brought into contact with the example device for 2 seconds before time-resolved OCT images were acquired. Five seconds into data acquisition the vacuum was activated, which may be clearly seen by an instantaneous change of decreased surface reflection. Throughout the following 7 seconds the image contrast between epidermal-dermal junction was noticeably increased. During the next 10 seconds, deeper layers within dermis become brighter. After the total time of approximately 20 seconds of vacuum maximum light transport into the in vivo tissue was obtained.

Figure 16B:
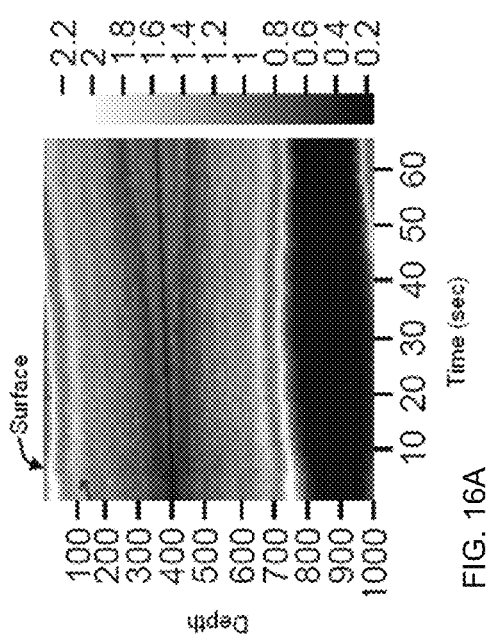
FIG. 16B is an OCT M-scan at 1310 nm wavelength illustrating in vivo human skin on palm of hand of Human Subject No. II which has been brought into contact with Example Device No. 1 under good vacuum conditions.

FIG. 16(b) shows the M-scan of the palm of the hand of subject II. In this experiment OCT data was acquired for 2 seconds, then the palm was brought into contact with the device for 3 seconds before the vacuum was turned on. Activation of the vacuum reduced surface reflection immediately. Similarly, within 3 seconds epidermal-dermal layer contrast was improved, followed by drastically enhanced deep image contrast within 6 seconds after activation of the vacuum. Since the stratum corneum may be much thicker on the palm of the hand compared to the volar forearm these results may be particularly encouraging and compare well to the above mentioned results.

Figure 17B:
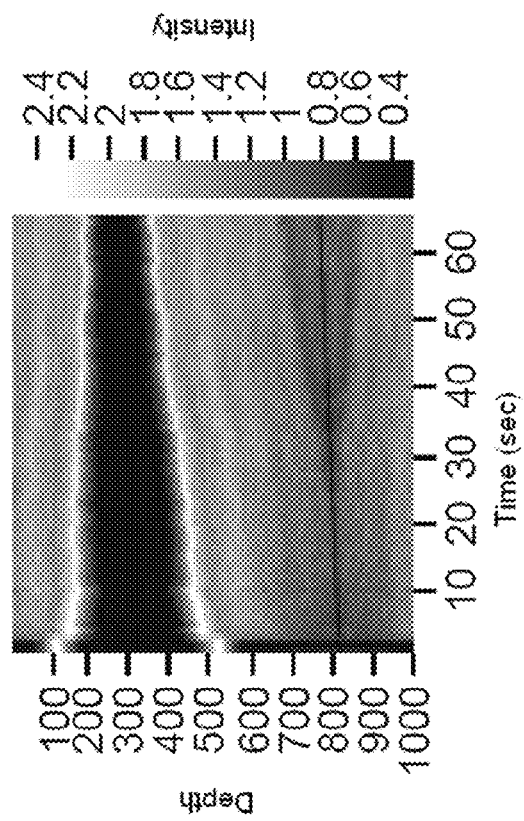
FIG. 17B is an OCT M-scan at 1310 nm wavelength illustrating in vivo human skin on volar forearm of Human Subject No. III which has been brought into contact with Example Device No. 1 under good vacuum conditions.
Figure 17A:
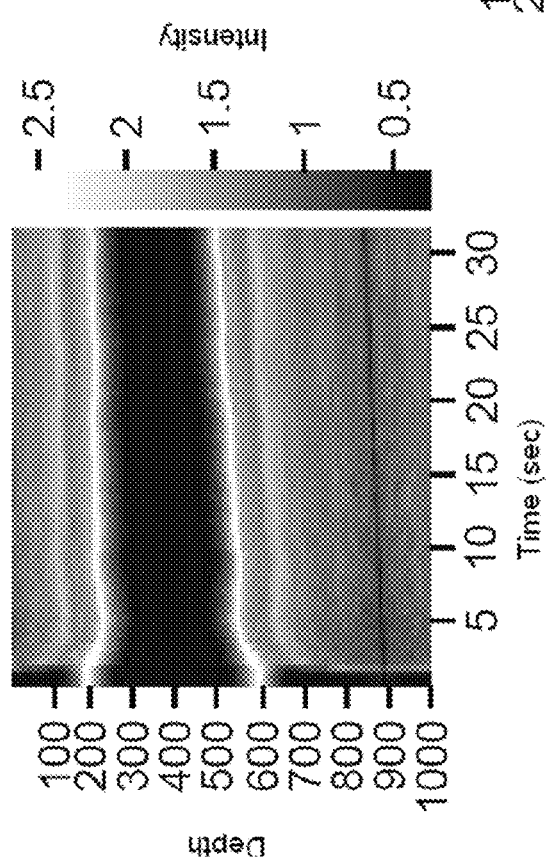
FIG. 17A is an OCT M-scan at 1310 nm wavelength illustrating in vivo human skin on top of hand of Human Subject No. III which has been brought into contact with Example Device No. 1 under partial vacuum conditions.

FIG. 17 shows M-scans of the top of the hand and volar forearm of human subject III. FIG. 17(a) was obtained by acquiring OCT data for 2 seconds before the top of the hand was brought into contact with the device. Two seconds after skin contact the vacuum was turned on. In this experiment however, there was some air leakage, which resulted in a partial vacuum of higher than normal pressure. Consequently, the surface reflection changes only slightly. After 8 seconds under partial vacuum deeper dermal features appear brighter. This transient trend continues throughout the following 30 seconds after which structures very deep within dermis start to appear. Thus, deep features within skin become visible as they did in previous experiments. In this case though, the partial vacuum slowed down the increased light transport roughly by a factor of two in comparison to experiments with fully established vacuum right from the beginning.

FIG. 17(b) shows the volar forearm of human subject III. Data acquisition and timing of skin contact and vacuum were the same as for part (a). With a properly sealed vacuum surface reflection decreases quickly after activation of the vacuum and dermal features become visible within 2 seconds after vacuum is established. Throughout the following 20 seconds deepest dermal features become visible with little change after seconds into the experiment.

Figure 18B:
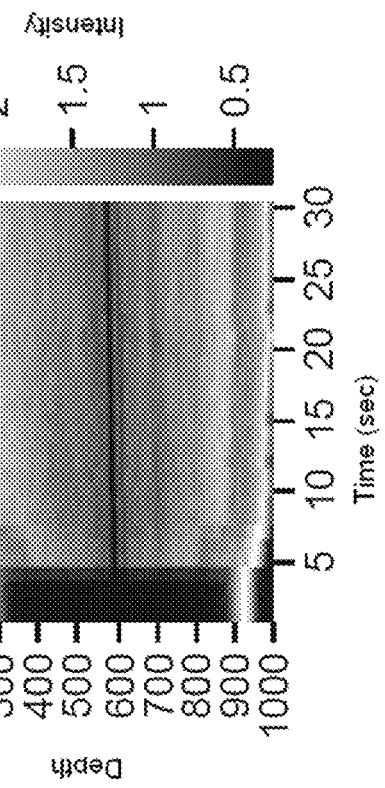
FIG. 18B is an OCT M-scan at 1310 nm wavelength illustrating in vivo human skin between thumb and index finger of Human Subject No. III which has been brought into contact with Example Device No. 1 under good vacuum conditions.
Figure 18A:
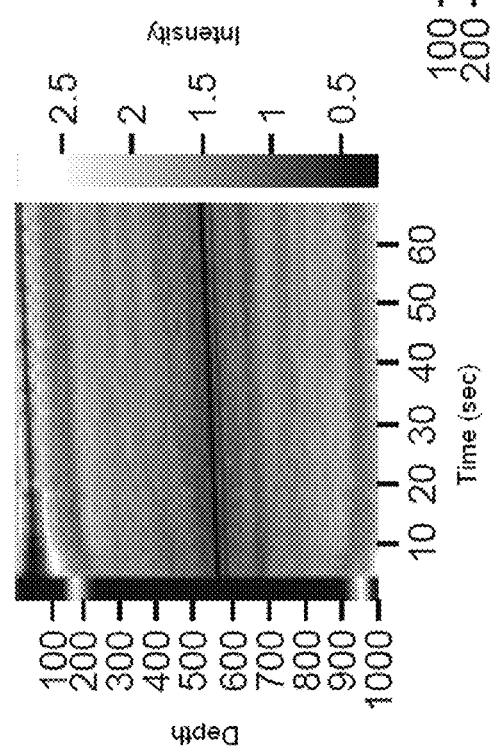
FIG. 18A is an OCT M-scan at 1310 nm wavelength illustrating in vivo human skin on volar wrist of Human Subject No. III which has been brought into contact with Example Device No. 1 under good vacuum conditions.

FIG. 18 shows OCT M-scans of the volar wrist and skin between thumb and index finger of human subject III. The wrist was imaged for 2 seconds prior to initial skin contact. Five seconds after skin contact the vacuum was established. Part (a) shows direct correlation between reduced surface reflection and activation of the vacuum. One to two seconds following the vacuum epidermal-dermal layer contrast was enhanced due to improved light transport. Deep dermal layers were fully visible 25 seconds after activation of the vacuum.

The skin between thumb and index finger of subject III was imaged in a similar manner. Data was acquired for 4 seconds before skin was brought into contact with device no. 1. Four seconds after skin contact was made the vacuum was activated. This again caused immediate improvement of epidermal-dermal contrast and within 8 seconds of vacuum influence deep dermal layers were fully visible as may be seen in FIG. 18(b).

Summarizing observations on time-resolved OCT scans all of the anatomical locations chosen show some improvement of light transport, but the volar forearm and wrist "optically clear" quickest and most effectively. When the vacuum does seal properly, most of the improvement in contrast occurs within 3-5 s, while the increased light reflection in deep layers occurs more slowly with little improvement beyond about 10 s. In case the vacuum does not seal properly, epidermal-dermal contrast does not improve significantly, but there may be usually a slight and slow increase in light reflection from deeper in the dermis.

Example 6

Thermal Infrared Measurements

Light transport through in vitro pig skin was evaluated using a thermal infrared measurement technique. A 980 nm diode laser was used to irradiate highly pigmented porcine skin. Absorption by hair follicles and melanin in the epidermis gives rise to a temperature change which was imaged using a thermal camera.

The laser was equipped with a scanning mechanism, allowing the 2 mm laser spot size to be scanned over an area up to 16 mm$^2$. Thermal images were acquired at a sampling rate of 20 Hz over a time frame of 10 seconds. Experiments were conducted by irradiating the tissue through the device. The experimental set-up is shown schematically in FIG. 19.

Experiments with two different configurations were carried out. In one case the Example Device No. 1 was applied to the highly pigmented epidermal side. This allowed monitoring of the temperature change on the dermal side where there may be hair follicles visible, cf. FIG. 11. Laser light was delivered into the tissue through the device and propagated through the ~2 mm thick pig skin tissue. Absorption of 980 nm laser energy by hair follicles gave rise to a temperature change as shown in FIG. 20(*a*).

Another configuration involved application of device no. 1 onto the dermal side of in vitro porcine skin of similar thickness. In this set-up 980 nm laser light was delivered through the device into dermis, allowing direct thermal imaging of light absorption leading to a temperature increase on the melanin-rich epidermal side of the tissue specimen. A single frame of the resulting temperature increase during the laser pulse is shown in FIG. 20(*b*).

FIGS. 20(*a*) and (*b*) may be the result of overlaying a thermal image of the pin device over the heat image of irradiated in vitro porcine skin. This technique allowed correlating pin location with improved heating of hair follicles as shown in FIG. 20(*a*) as well as improved local heating of epidermal melanin as shown in FIG. 20(*b*). Here, light was transmitted through the device into dermis, which then permitted direct visualization of epidermal heating—redundant from above. The white box marked the laser scan range and locally higher temperatures were obtained. These regions of enhanced epidermal heating correlate directly with the pin geometry. Thus, the data shows improved light transport through the device.

Example 7

A Tissue Optical Clearing and Cooling Device

1) TOCC Device

A Tissue Optical Clearing/Cooling (TOCC) device may consist of an array of pins, radiant filters, inlet and exit ports for vacuum and cooling, and a laser handpiece interface tab. See FIGS. 4B and 6A-6F. The device may be constructed of lexan. Lexan is a transparent, Food and Drug Administration-approved polymer which may be manufactured by injection molding. The device may be integrated with existing laser handpieces. A TOCC device may contact the skin for a few seconds inducing optical clearing and cooling, and subsequently laser radiation may be transmitted through the device.

An array of pins may comprise the inner surface of the TOC device and may provide mechanical force on the skin. Pin design parameters may include pin shape, diameter, length, arrangement, number, and area fraction. Pins may be rounded, may have a uniform diameter, and may have a hexagonal packing arrangement. Pin diameters of 0.7 to 1.0 mm may be used to maximize flux of water transport in response to tissue compression and provide fast (1-5 s) response of tissue optical property change. Pin length of about 2-3 mm and pin packing densities of 20%-30% may be used. A brim along the periphery of the device may form an airtight vacuum seal with the tissue surface. The length and width of the brim may be approximately the same as that of the pins.

Radiant filters may be utilized to control spatial and angular distribution of incident radiant energy into targeted tissue regions. Radiant filters may be structurally embodied as lenses on the posterior side of the pin array device. Lenses may permit angular control (focusing or divergence) of radiant energy incident on the tissue. Radiant filters may be designed to focus all radiant light at a target depth in the dermis. For example, to target the adipose layer, radiant filters may be configured to focus light 2 mm beneath the skin surface. This target depth may be varied according to the treatment objective of a particular condition.

Inlet and exit ports may permit integration of vacuum and cooling systems with a Tissue Optical Clearing (TOC) device and tissue surface. A vacuum system may aid in the optical clearing process by forcing the tissue against the pins while simultaneously pulling tissue into the volume surrounding each pin. A cooling system will provide tissue surface cooling and prevention of thermal damage to non-targeted superficial layers before, during, or after entry of radiant energy into the tissue.

A handpiece interface tab may provide a mechanical linkage between the TOC device and the laser handpiece, as shown in FIGS. 6E-6F. A draw latch and keeper system will provide a good interface between the laser handpiece and the TOC device. For example, it may allow clinicians to quickly and easily snap the device on and off. The handpiece interface tab is structurally embodied as a keeper which accepts the latch (built into the laser handpiece) with a flanged or curved tip.

2) Vacuum System

A vacuum device may aid in the mechanical transduction process by forcing the tissue against the pins while simultaneously pulling tissue into the volume surrounding each pin. The increased tissue volume surrounding the pins (expanded tissue regions) may provide additional storage capacity for water and blood displaced from under the pins. A vacuum device may include a vacuum pump and a hose connecting the pump to the pin array device. See FIG. 4B.

3) Cooling System

A cooling system may provide tissue surface cooling and may prevent thermal damage to non-targeted superficial layers before, during, and/or after entry of radiant energy into the tissue. The device may be structurally embodied as a cavity with one open side which may be placed against a tissue (such as skin), resulting in the formation of a closed chamber. A cold fluid may be injected into the chamber from several possible sources: liquid or gas cryogen such as R-134a, nitrogen, oxygen, or a mixture of gases (e.g., air). Temperature of gas, such as air, may be reduced using a heat pump or a Ranque-Hilsch vortex tube. Removal of water vapor from gas may be necessary to prevent heat pump or vortex tube malfunction and may be accomplished using water removal filters or desiccant driers. Injection and removal of cold fluid from the cooling chamber may be regulated with an inlet and exit solenoid valve. Vacuum pump connected downstream of the exit valve may help seal the device against the tissue surface and enhance the fluid flow and therefore performance of the cooling procedure. Increasing the velocity and turbulence of cold fluid injected into the chamber may escalate heat loss from tissue.

The foregoing description and examples describe some embodiments of the disclosure. Artisans of ordinary skill will recognize that other embodiments may be within the contemplation of the present disclosure. For example, systems and devices of the disclosure may be configured to be sanitizable, sterilizable, disposable, repairable, disposable, and/or reusable. In addition, a plurality of optical clearing devices may be used on a single subject simultaneously or sequentially. Moreover, one of ordinary skill in the art will appreciate that no embodiment, use, and/or advantage may be intended to universally control or exclude other embodiments, uses, and/or advantages. Accordingly, the foregoing disclosure is intended to be illustrative, but not limiting, of the scope of the disclosure.

What is claimed is:

1. An optical clearing device for tissue comprising:
    a mechanical transducer adapted for contacting tissue and operable for applying a mechanical force to a region of tissue;
    a tissue position and hold component operable to maintain the mechanical force applied to the region of tissue and create at least one indentation of at least 0.1 mm in depth in the tissue;
    a feedback system comprising a control unit operably coupled with the tissue position and hold component and at least one sensor that provides a feedback signal to the control unit signaling tissue thickness that is altered to at least 0.1 mm in depth beneath the at least one indentation relative to the tissue surrounding the at least one indentation; and in response to the feedback signal the control unit signals the tissue position and hold component that the at least one indentation persists in the tissue for at least 10 seconds after the mechanical transducer is removed from the tissue; and
    a radiant source configured to illuminate at least a portion of the optical clearing device with at least one wavelength of light.

2. An optical clearing device according to claim 1, wherein at least a portion of the device is transparent to at least one wavelength of light.

3. An optical clearing device according to claim 2, wherein the transparent portion comprises a material selected from the group consisting of glass, clear plastic resin, a crystalline material, sapphire, and diamond.

4. An optical clearing device according to claim 2, wherein the optical clearing device is configured and arranged to be wearable by a human and/or a non-human mammal.

5. An optical clearing device according to claim 1, wherein the tissue position and hold component comprises a brim fixed surrounding the mechanical transducer, wherein, the brim, the mechanical transducer, and the tissue define a chamber; an inlet port to permit a flow of fluid or gas into the chamber; and an exit port to permit a flow of fluid or gas exiting the chamber.

6. An optical clearing device according to claim 5, wherein the mechanical transducer comprises an array of pins.

7. An optical clearing device according to claim 6, wherein the diameter of at least one pin is from about 0.5 mm to about 1.0 mm.

8. An optical clearing device according to claim 6, wherein the length of at least one pin is from about 2.0 mm to about 3.0 mm.

9. An optical clearing device according to claim 6, wherein the packing density of pins is greater than about 20%.

10. An optical clearing device according to claim 6, wherein at least one pin comprises the radiant source.

11. An optical clearing device according to claim 10, wherein at least one pin comprises a radiant filter.

12. An optical clearing device according to claim 5, wherein the brim is laterally offset from the edge of the pin array.

13. An optical clearing device according to claim 5, wherein the brim is about the same length as at least one pin.

14. An optical clearing device according to claim 1, further comprising a radiant filter.

15. A system for treating a tissue comprising an optical clearing device comprising a substantially planar base, an array of pins, a brim, an inlet port, and an exit, wherein the base comprises at least two opposing sides, the array of pins is fixed to one side of the base, the brim is fixed to the same side of the base as the array of pins, the inlet port is in the base and is in fluid communication with both sides of the base, the exit port is in the base and is in fluid communication with both sides of the base
    a radiant source configured to illuminate at least a portion of the optical clearing device with at least one wavelength of light;
    a radiant filter in optical communication with the radiant source and the optical clearing device; and
    a vacuum device in fluid communication with the inlet port of the optical clearing device and configured to draw a sufficient vacuum to create at least one indentation in the tissue by a radiant energy feedback mechanism comprising a control unit operably coupled to the vacuum device and at least one sensor element that provides a feedback signal to the control unit signaling tissue thickness that is altered to at least 0.1 mm in depth beneath the at least one indentation relative to the tissue surrounding the at least one indentation; and in response to the feedback signal to the control unit stops the vacuum device such that the at least one indentation persists in the tissue for at least 10 seconds after the array of pins are removed from the tissue.

16. A system according to claim 15, further comprising a cooling system comprising a thermally controlled fluid in thermal contact with at least the optical clearing device and a thermal controller in thermal contact with at least the thermally-controlled fluid; and wherein the brim is fixed to the base along the perimeter of the base.

17. A system according to claim 15, wherein the radiant source is selected from the group consisting of a laser, a radio frequency source, a microwave source, an x-ray source, and an incoherent light source such as a light emitting diode or flashlamp source.

18. A system according to claim 15, wherein the radiant energy feedback mechanism comprising:
    the at least one sensor element is at least one optical sensor configured and arranged to assess the fluence, wavelength, scattering, or absorbance of radiant energy in the tissue; a processor (a) in communication with the at least one optical sensor and (b) configured and arranged to process optical sensor input and assess satisfaction of a pre-selected condition; and
    a controller in communication with the processor and configured and arranged to modify the fluence, wavelength, scattering, or absorbance of radiant energy in the tissue.

19. An optical clearing device for tissue comprising:
a substantially planar base;
an array of pins fixed to one side of the base to contact the tissue create to at least one indentation in the tissue by a feedback system comprising a control unit operably coupled to the array of pins and at least one sensor element that provides a feedback signal to the control unit signaling tissue thickness that is altered to at least 0.1 mm in depth beneath the at least one indentation relative to the tissue surrounding the at least one indentation, and in response to the feedback signal the control unit stops the contact of the array of pins to the tissue such that the at least one indentation persists in the tissue for at least 10 seconds after the array of pins are removed from the tissue;
a brim fixed to the base and surrounding the array of pins, wherein, in use, the base, the brim and the tissue define a chamber;
an inlet port in the base to permit a flow of fluid or gas into the chamber;
an exit port in the base to permit a flow of fluid or gas exiting the chamber.

\* \* \* \* \*

UNITED STATES PATENT AND TRADEMARK OFFICE
CERTIFICATE OF CORRECTION

PATENT NO. : 9,168,388 B2  
APPLICATION NO. : 13/693974  
DATED : October 27, 2015  
INVENTOR(S) : Christopher G. Rylander et al.

Page 1 of 1

It is certified that error appears in the above-identified patent and that said Letters Patent is hereby corrected as shown below:

IN THE SPECIFICATION

Column 1 lines 15-18 should read

STATEMENT OF GOVERNMENT SUPPORT

This invention was made with government support under Grant No. 9870653 and Grant No. 9986296 awarded by the National Science Foundation and Grant No. AR047551 awarded by the National Institutes of Health. The government has certain rights in the invention.

Signed and Sealed this  
First Day of March, 2016

Michelle K. Lee  
*Director of the United States Patent and Trademark Office*